(12) United States Patent
Albrecht et al.

(10) Patent No.: US 10,577,350 B2
(45) Date of Patent: Mar. 3, 2020

(54) CRYSTALLINE FORMS OF (R)-N-((4-METHOXY-6-METHYL-2-OXO-1,2-DIHYDROPYRIDIN-3-YL)METHYL)-2-METHYL-1-(1-(1-(2,2,2-TRIFLUOROETHYL) PIPERIDIN-4-YL)ETHYL)-1H-INDOLE-3-CARBOXAMIDE

(71) Applicant: Constellation Pharmaceuticals, Inc., Cambridge, MA (US)

(72) Inventors: Brian K. Albrecht, Cambridge, MA (US); Alisha Arrigo, Boulder, CO (US); Donald Corson, Boulder, CO (US); Victor S. Gehling, Somerville, MA (US); Bruno Patrice Haché, Longmont, CO (US); Jean-Christophe Harmange, Andover, MA (US); Jonathan Lane, Longmont, CO (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/755,854

(22) PCT Filed: Aug. 25, 2016

(86) PCT No.: PCT/US2016/048616
§ 371 (c)(1),
(2) Date: Feb. 27, 2018

(87) PCT Pub. No.: WO2017/040190
PCT Pub. Date: Mar. 9, 2017

(65) Prior Publication Data
US 2018/0327386 A1    Nov. 15, 2018

Related U.S. Application Data

(60) Provisional application No. 62/211,383, filed on Aug. 28, 2015.

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC .................................................. C07D 401/14
See application file for complete search history.

(56) References Cited

U.S. PATENT DOCUMENTS

| | | |
|---|---|---|
| 4,738,971 A | 4/1988 | Eriksoo et al. |
| 5,308,854 A | 5/1994 | Hoffman, Jr. et al. |
| 7,838,520 B2 | 11/2010 | Delorme et al. |
| 8,410,088 B2 | 4/2013 | Kuntz et al. |
| 8,536,179 B2 | 9/2013 | Miller et al. |
| 8,846,935 B2 | 9/2014 | Duquenne et al. |
| 9,051,269 B2 | 6/2015 | Albrecht et al. |
| 9,085,583 B2 | 7/2015 | Albrecht et al. |
| 9,206,128 B2 | 12/2015 | Albrecht et al. |
| 9,371,331 B2 | 6/2016 | Albrecht et al. |
| 9,374,093 B2 | 6/2016 | Pelley et al. |
| 9,409,865 B2 | 8/2016 | Albrecht et al. |
| 9,469,646 B2 | 10/2016 | Albrecht et al. |
| 9,969,716 B2 | 5/2018 | Albrecht et al. |
| 2003/0207875 A1 | 11/2003 | Gymer et al. |
| 2003/0229081 A1 | 12/2003 | Maduskuie |
| 2004/0186138 A1 | 9/2004 | Annoura et al. |
| 2005/0266473 A1 | 12/2005 | Zhang et al. |
| 2006/0035938 A1 | 2/2006 | Bladh et al. |
| 2007/0155744 A1 | 7/2007 | Jones et al. |
| 2008/0027050 A1 | 1/2008 | Terauchi et al. |
| 2008/0227826 A1 | 9/2008 | Frechette et al. |
| 2008/0280917 A1 | 11/2008 | Albrecht et al. |
| 2009/0029991 A1 | 1/2009 | Stokes et al. |
| 2009/0075833 A1 | 3/2009 | Chinnaiyan et al. |
| 2009/0270361 A1 | 10/2009 | Ito et al. |

(Continued)

FOREIGN PATENT DOCUMENTS

| | | |
|---|---|---|
| WO | 2003/020722 A1 | 3/2003 |
| WO | 2003/079986 A2 | 10/2003 |

(Continued)

OTHER PUBLICATIONS

Sakurai. Biochemical and Biophysical Research Communications, 2012, 422, 603-14 (Year: 2012).*

(Continued)

*Primary Examiner* — Noble E Jarrell

(74) *Attorney, Agent, or Firm* — McCarter & English, LLP; Steven G. Davis; Michael J. DeGrazia

(57) ABSTRACT

The present disclosure relates to a crystalline Forms A, B, and C of (R)—N-((4-methoxy-6-methyl-2-oxo-1,2-di-hy-dropyridin-3-yl)methyl)-2-methyl-1-(1-(1-(2,2,2-trifluoro-ethyl)piperidin-4-yl)ethyl)-1H-indole-3-carboxamide, each of which are useful as modulators the activity of histone methyl modifying enzymes. The present disclosure also provides pharmaceutically acceptable compositions comprising the crystalline forms and methods of using said compositions in the treatment of various disorders.

(I)

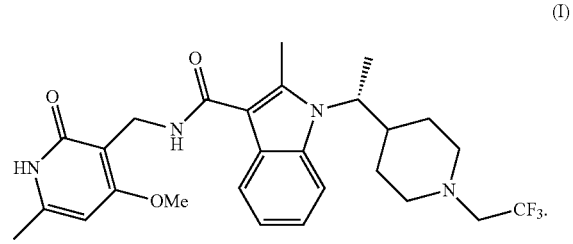

15 Claims, 12 Drawing Sheets

(56) References Cited

U.S. PATENT DOCUMENTS

| | | | |
|---|---|---|---|
| 2010/0069630 | A1 | 3/2010 | Lee et al. |
| 2010/0222420 | A1 | 9/2010 | Chinnaiyan et al. |
| 2010/0261743 | A1 | 10/2010 | Londregan et al. |
| 2010/0298270 | A1 | 11/2010 | Keana et al. |
| 2011/0105509 | A1 | 5/2011 | Kaila et al. |
| 2011/0212946 | A1 | 9/2011 | Barrow et al. |
| 2012/0071418 | A1 | 3/2012 | Copeland et al. |
| 2012/0264734 | A1 | 10/2012 | Kuntz et al. |
| 2013/0040906 | A1 | 2/2013 | Kuntz et al. |
| 2013/0230511 | A1 | 9/2013 | Heymach et al. |
| 2013/0310379 | A1 | 11/2013 | Albrecht et al. |
| 2014/0107122 | A1 | 4/2014 | Kuntz et al. |
| 2014/0142083 | A1 | 5/2014 | Kuntz et al. |
| 2015/0011546 | A1 | 1/2015 | Albrecht et al. |
| 2015/0368229 | A1 | 12/2015 | Albrecht et al. |
| 2015/0376190 | A1 | 12/2015 | Albrecht et al. |
| 2016/0009718 | A1 | 1/2016 | Albrecht et al. |
| 2016/0185757 | A1 | 6/2016 | Albrecht et al. |
| 2016/0333016 | A1 | 11/2016 | Albrecht et al. |
| 2017/0056388 | A1 | 3/2017 | Albrecht et al. |
| 2018/0037568 | A1 | 2/2018 | Albrecht et al. |

FOREIGN PATENT DOCUMENTS

| | | | |
|---|---|---|---|
| WO | 2007/011626 | A2 | 1/2007 |
| WO | 2007/014838 | A1 | 2/2007 |
| WO | 2007/067968 | A2 | 6/2007 |
| WO | 2009/006577 | A2 | 1/2009 |
| WO | 2009/058102 | A1 | 5/2009 |
| WO | 2009/087285 | A1 | 7/2009 |
| WO | 2009/153721 | A1 | 12/2009 |
| WO | 2011/131741 | A1 | 10/2011 |
| WO | 2011/140324 | A1 | 11/2011 |
| WO | 2011/140325 | A1 | 11/2011 |
| WO | 2012/005805 | A1 | 1/2012 |
| WO | 2012/024543 | A1 | 2/2012 |
| WO | 2012/051492 | A2 | 4/2012 |
| WO | 2012/068589 | A2 | 5/2012 |
| WO | 2012/075080 | A1 | 6/2012 |
| WO | 2012/115885 | A1 | 8/2012 |
| WO | 2012/118812 | A2 | 9/2012 |
| WO | 2013/039988 | A1 | 3/2013 |
| WO | 2013/049770 | A2 | 4/2013 |
| WO | 2013/067296 | A1 | 5/2013 |
| WO | 2013/067300 | A1 | 5/2013 |
| WO | 2013/067302 | A1 | 5/2013 |
| WO | 2013/075083 | A1 | 5/2013 |
| WO | 2013/075084 | A1 | 5/2013 |
| WO | 2013/078320 | A1 | 5/2013 |
| WO | 2013/120104 | A2 | 8/2013 |
| WO | 2013/138361 | A1 | 9/2013 |
| WO | 2013/155317 | A1 | 10/2013 |
| WO | 2013/155464 | A1 | 10/2013 |
| WO | 2013/173441 | A2 | 11/2013 |
| WO | 2014/049488 | A1 | 4/2014 |
| WO | 2014/062720 | A2 | 4/2014 |
| WO | 2014/062733 | A2 | 4/2014 |
| WO | 2014/071109 | A1 | 5/2014 |
| WO | 2014/077784 | A1 | 5/2014 |
| WO | 2014/085666 | A1 | 6/2014 |
| WO | 2014/092905 | A1 | 6/2014 |
| WO | 2014/097041 | A1 | 6/2014 |
| WO | 2014/100080 | A1 | 6/2014 |
| WO | 2014/124418 | A1 | 8/2014 |
| WO | 2014/151142 | A1 | 9/2014 |
| WO | 2015/023915 | A1 | 2/2015 |
| WO | 2015/085325 | A1 | 6/2015 |
| WO | 2015/200650 | A1 | 12/2015 |
| WO | 2016/130396 | A1 | 8/2016 |

OTHER PUBLICATIONS

Takawa. Cancer Science, 2011, 102 (7), 1298-1305 (Year: 2011).*
Hock. Genes and Development, 2012, 26, 751-55 (Year: 2012).*
U.S. Appl. No. 14/377,214, filed Aug. 7, 2014, U.S. Pat. No. 9,085,583, Granted.
U.S. Appl. No. 14/661,797, filed Mar. 18, 2015, U.S. Pat. No. 9,371,331, Granted.
U.S. Appl. No. 15/155,749, filed May 16, 2016, US-2017-0312262-A9, Allowed.
U.S. Appl. No. 15/962,150, filed Apr. 25, 2018, Pending.
U.S. Appl. No. 14/766,632, filed Aug. 7, 2015, US-2015-0376190-A1, Abandoned.
U.S. Appl. No. 14/839,273, filed Aug. 28, 2015, U.S. Pat. No. 9,469,646, Granted.
U.S. Appl. No. 15/257,275, filed Sep. 6, 2016, US-2017-0056388-A1, Allowed.
U.S. Appl. No. 15/878,663, filed Jan. 24, 2018, Reissue Pending.
Abreu et al., DNA methylation: a promising target for the twenty-first century. Expert Opin Ther Targets. Aug. 2008;12(8):1035-47.
Amatangelo et al., Three-dimensional culture sensitizes epithelial ovarian cancer cells to EZH2 methyltransferase inhibition. Cell Cycle. Jul. 1, 2013;12(13):2113-9.
Aref et al., Regulatory T cells in chronic lymphocytic leukemia. Comp Clin Pathol. 2015;24:649-652.
Balasubramanian et al., CPI-169, a novel and potent EZH2 inhibitor, synergizes with CHOP in vivo and achieves complete regression in lymphoma xenograft models. AACR Annual Meeting, Cancer Research. Oct. 1, 2014;74(19 Suppl):Abstract 1697. 2 pages.
Bradley et al., EZH2 inhibitor efficacy in non-Hodgkin's lymphoma does not require suppression of H3K27 monomethylation. Chemistry & Biology. Nov. 20, 2014;21:1463-1475.
Bradley et al., Inhibitors of EZH2 act synergistically with type 1 interferon to induce a potent interferon-stimulated gene response, triggering apoptosis in diffuse large B-cell lymphoma. European Journal of Cancer. 2014;50(Suppl 6):125, Poster 390. 1 page.
Caira, Crystalline Polymorphism of Organic Compounds. Topics in Current Chemistry. Springer Verlag, Berlin. 1998;198:163-208.
CAS Registry No. 1061629-12-6.
CAS Registry No. 1100242-53-2.
CAS Registry No. 1118826-71-3.
CAS Registry No. 1269034-31-2.
CAS Registry No. 1269039-62-4.
CAS Registry No. 1278089-62-5.
CAS Registry No. 1290560-58-5.
Chase et al., Aberrations of EZH2 in cancer. Clin Cancer Res. May 1, 2011;17(9):2613-8.
Fiskus et al., Combined epigenetic therapy with the histone methyltransferase EZH2 inhibitor 3-deazaneplanocin A and the histone deacetylase inhibitor panobinostat against human AML cells. Blood. Sep. 24, 2009;114(13):2733-43.
Fiskus et al., Combined Targeting of Chromatin Modifying Enzymes LSD1, EZH2 and Histone Deacetylases (HDACs) Has Superior Efficacy Against Human Mantle Cell Lymphoma Cells. Blood. 2011;118(21):Abstract 2429. 2 pages.
Fiskus et al., Histone deacetylase inhibitors deplete enhancer of zeste 2 and associated polycomb repressive complex 2 proteins in human acute leukemia cells. Mol Cancer Ther. Dec. 2006;5(12):3096-104.
Fozza et al., Derangement of the T-cell repertoire in patients with B-cell non-Hodgkin's lymphoma. Eur J Haematol. Apr. 2015;94(4):298-309.
Gehling et al., Discovery, design, and synthesis of indole-based EZH2 inhibitors. Bioorg Med Chem Lett. Sep. 1, 2015;25(17):3644-9.
Gillet et al., The clinical relevance of cancer cell lines. J Natl Cancer Inst. Apr. 3, 2013;105(7):452-8.
Gupta et al., SHP1 Suppression in Diffuse Large B Cell Lymphoma Is Regulated Through Promoter Hypermethylation At Novel CpG2 Island and H3K27 Trimethylation Histone Mark. Blood. 2013;122:Abstract 632. 2 pages.
Gura, Systems for identifying new drugs are often faulty. Science. Nov. 7, 1997;278(5340):1041-2.
Ito et al., A medium-term rat liver bioassay for rapid in vivo detection of carcinogenic potential of chemicals. Cancer Sci. Jan. 2003;94(1):3-8.

(56) References Cited

OTHER PUBLICATIONS

Johnson et al., Relationships between drug activity in NCI preclinical in vitro and in vivo models and early clinical trials. Br J Cancer. May 18, 2001;84(10):1424-31.
Knutson et al., A selective inhibitor of EZH2 blocks H3K27 methylation and kills mutant lymphoma cells. Nat Chem Biol. Nov. 2012;8(11):890-6.
Knutson et al., Durable tumor regression in genetically altered malignant rhabdoid tumors by inhibition of methyltransferase EZH2. Proc Natl Acad Sci U S A. May 7, 2013;110(19):7922-7.
Knutson et al., Selective inhibition of EZH2 by EPZ-6438 leads to potent antitumor activity in EZH2-mutant non-Hodgkin lymphoma. Mol Cancer Ther. Apr. 2014;13(4):842-54.
Knutson et al., Synergistic Anti-Tumor Activity of EZH2 Inhibitors and Glucocorticoid Receptor Agonists in Models of Germinal Center Non-Hodgkin Lymphomas. PLoS One. Dec. 10, 2014;9(12):e111840. 22 pages.
Kondo, Targeting histone methyltransferase EZH2 as cancer treatment. J Biochem. Nov. 2014;156(5):249-57.
Konze et al., An orally bioavailable chemical probe of the Lysine Methyltransferases EZH2 and EZH1. ACS Chem Biol. 2013;8(6):1324-34.
McCabe et al., EZH2 inhibition as a therapeutic strategy for lymphoma with EZH2-activating mutations. Nature. Dec. 6, 2012;492(7427):108-12.
National Cancer Institute. Seer Training Modules. Cancer Classification. Retrieved online at: http://training.seer.cancer.gov/module_ase/unit3_categories2_by_histology.html. 3 pages. (2012).
Peng et al., Epigenetic silencing of Th1-type chemokines dictates effector T cell tumor trafficking and predicts patient outcome (TUM7P.1019). The Journal of Immunology. May 1, 2015;194(1):Abstract 142.8, 1 page.
Peng et al., Epigenetic silencing of TH1-type chemokines shapes tumour immunity and immunotherapy. Nature. Nov. 12, 2015;527(7577):249-53.
PubChem Compound Summary for CID 40170690, May 30, 2009, 2 pages.
PubChem Compound Summary for CID 50961558, Mar. 29, 2011, 2 pages.
PubChem Compound Summary for CID 6918837, Jul. 28, 2006, 2 pages.
PubChem Compound Summary for CID 73087, Aug. 1, 2005, 2 pages.
Qi et al., Selective inhibition of Ezh2 by a small molecule inhibitor blocks tumor cells proliferation. Proc Natl Acad Sci U S A. Dec. 26, 2012;109(52):21360-5.
Registry, May 25, 2011, RN: 1300453-83-1.
Registry, Sep. 1, 2011, RN: 1326727-17-6.
Registry, Sep. 2, 2011, RN: 1327055-57-1.
Registry, Sep. 29, 2011, RN: 1333889-30-7.
Registry, Sep. 4, 2011, RN: 1328132-30-4.
Registry, Sep. 5, 2011, RN: 1328462-28-7.
Registry, Sep. 6, 2011, RN 1328976-87-9.
Registry, Sep. 7, 2011, RN 1329352-49-9.
Registry, Sep. 7, 2011, RN: 1329234-68-5.
Roy et al., Role of bacterial infection in the epigenetic regulation of Wnt antagonist WIF1 by PRC2 protein EZH2. Oncogene. Aug. 20, 2015;34(34):4519-30.
Sasaki et al., Overexpression of Enhancer of zeste homolog 2 with trimethylation of lysine 27 on histone H3 in adult T-cell leukemia/lymphoma as a target for epigenetic therapy. Haematologica. May 2011;96(5):712-9.
Shang et al., Prognostic value of tumor-infiltrating FoxP3+ regulatory T cells in cancers: a systematic review and meta-analysis. Sci Rep. Oct. 14, 2015;5:15179. 9 pages.
Simone, Introduction. Omenn, Cancer Prevention. Part XIV, Oncology. Cecil Textbook of Medicine. 20th Edition, vol. 1. J. Claude Bennett (Ed.). W.B. Saunders Company. pp. 1004-1010. (1966).
Spannhoff et al., The emerging therapeutic potential of histone methyltransferase and demethylase inhibitors. ChemMedChem. Oct. 2009;4(10):1568-82.
STN registry database compound 1002886-67-0 from the ZINC (Soichet Laboratory) (entered STN on Feb. 12, 2008).
STN registry database compound 322425-80-9 (entered STN on Feb. 20, 2001).
STN registry database compound 950111-40-7 from Chemical Library Supplier Enamine (entered STN on Oct. 10, 2007).
Van Aller et al., Long residence time inhibition of EZH2 in activated polycomb repressive complex 2. ACS Chem Biol. Mar. 21, 2014;9(3):622-9.
Vazquez, Optimization of personalized therapies for anticancer treatment. BMC Syst Biol. Apr. 12, 2013;7:31. 11 pages.
Venkatesh et al., Role of the development scientist in compound lead selection and optimization. J Pharm Sci. Feb. 2000;89(2):145-54.
Verma et al., Identification of Potent, Selective, Cell-Active Inhibitors of the Histone Lysine Methyltransferase EZH2. ACS Med Chem Lett. Oct. 19, 2012;3(12):1091-6.
Williams et al., Foye's Principles of Medicinal Chemistry, 5th edition, Lippincott Williams & Wilkins. pp. 50, 59-61, (2002).
Woo et al., Biological evaluation of tanshindiols as EZH2 histone methyltransferase inhibitors. Bioorg Med Chem Lett. Jun. 1, 2014;24(11):2486-92.
Wu et al., Ezh2 lines up the chromatin in T regulatory cells. Immunity. Feb. 17, 2015;42(2):201-203.
Yamaguchi et al., Histone deacetylase inhibitor (SAHA) and repression of EZH2 synergistically inhibit proliferation of gallbladder carcinoma. Cancer Sci. Feb. 2010;101(2):355-62.
Yang et al., EZH2 is crucial for both differentiation of regulatory T cells and T effector cell expansion. Sci Rep. Jun. 19, 2015;5:10643. 14 pages.
Yap et al., Somatic mutations at EZH2 Y641 act dominantly through a mechanism of selectively altered PRC2 catalytic activity, to increase H3K27 trimethylation. Blood. Feb. 24, 2011;117(8):2451-9.
Yu, Amorphous pharmaceutical solids: preparation, characterization and stabilization. Adv Drug Deliv Rev. May 16, 2001;48(1):27-42.
Zhang et al., Reversing Metabolic and Epigenetic Cellular Alterations to Overcome Chemo-Resistance in Aggressive B Cell Lymphomas. Blood. 2012;120:Abstract 1305. 2 pages.
Copending Reissue U.S. Appl. No. 15/878,663, filed Jan. 24, 2018.
Copending Reissue U.S. Appl. No. 15/962,150, filed Apr. 25, 2018.

* cited by examiner

CRYSTALLINE FORMS OF (R)-N-((4-METHOXY-6-METHYL-2-OXO-1,2-DIHYDROPYRIDIN-3-YL)METHYL)-2-METHYL-1-(1-(1-(2,2,2-TRIFLUOROETHYL)PIPERIDIN-4-YL)ETHYL)-1H-INDOLE-3-CARBOXAMIDE

RELATED APPLICATIONS

This application is a U.S. national stage filing under 35 U.S.C. § 371 based on International Application No. PCT/US2016/048616, filed Aug. 25, 2016, which claims priority to U.S. Provisional Application No. 62/211,383, filed Aug. 28, 2015, the entire contents of each of which are incorporated herein by reference.

TECHNICAL FIELD OF THE INVENTION

Provided herein are crystalline forms of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, processes for preparing the crystalline forms, pharmaceutical compositions comprising the crystalline forms, and uses of the crystalline forms and compositions thereof in modulating the activity of histone methyl modifying enzymes.

BACKGROUND OF THE INVENTION

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

One class of histone methylases is characterized by the presence of a Suppressor of Variegation Enhancer of Zeste Trithorax (SET) domain, comprising about 130 amino acids. Enhancer of Zeste Homolog 2 (EZH2) is an example of a human SET-domain containing methylase. EZH2 associates with EED (Embryonic Ectoderm Development) and SUZ12 (suppressor of zeste 12 homolog) to form a complex known as PRC2 (Polycomb GroupRepressive Complex 2) having the ability to tri-methylate histone H3 at lysine 27 (Cao and Zhang, Mol. Cell 15:57-67, 2004). PRC2 complexes can also include RBAP46 and RBAP48 subunits. Another example is the related methylase EZH1.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor suppressors, including E-cadherin, DAB2IP and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

(R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide is an inhibitor of EZH2 and is useful in treating a variety of diseases, disorders or conditions, associated with a methyl modifying enzyme, such as, e.g., in treating proliferative disorders such as cancer.

The amorphous form of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide is exemplified in U.S. Patent Publication No. 2015/0011546 as Compound 365, and is incorporated herein by reference. (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide is represented by the following structural formula:

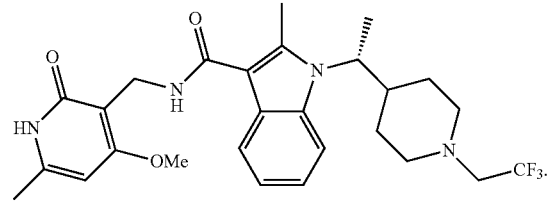 [SMILES: COc1cc(C)[nH]c(=O)c1CNC(=O)c1c(C)n([C@H](C)C2CCN(CC(F)(F)F)CC2)c2ccccc12]

Given the therapeutic benefits associated with the amorphous form, there is a need for the identification, characterization, manufacturing and development of crystalline forms of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide. Crystalline forms represent an attractive alternative to amorphous solids in that they facilitate isolation, manufacturing, formulation and enhance storage stability

SUMMARY OF THE INVENTION

Provided herein are novel crystalline Forms A, B, and C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide.

Also provided herein are pharmaceutical compositions comprising the crystalline Forms A, B, and C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, methods for their manufacture, and uses thereof for treating a variety of diseases, disorders or conditions associated with a methyl modifying enzyme, such as, e.g., in treating proliferative disorders such as cancer.

DETAILED DESCRIPTION

Definitions

Figure 1:
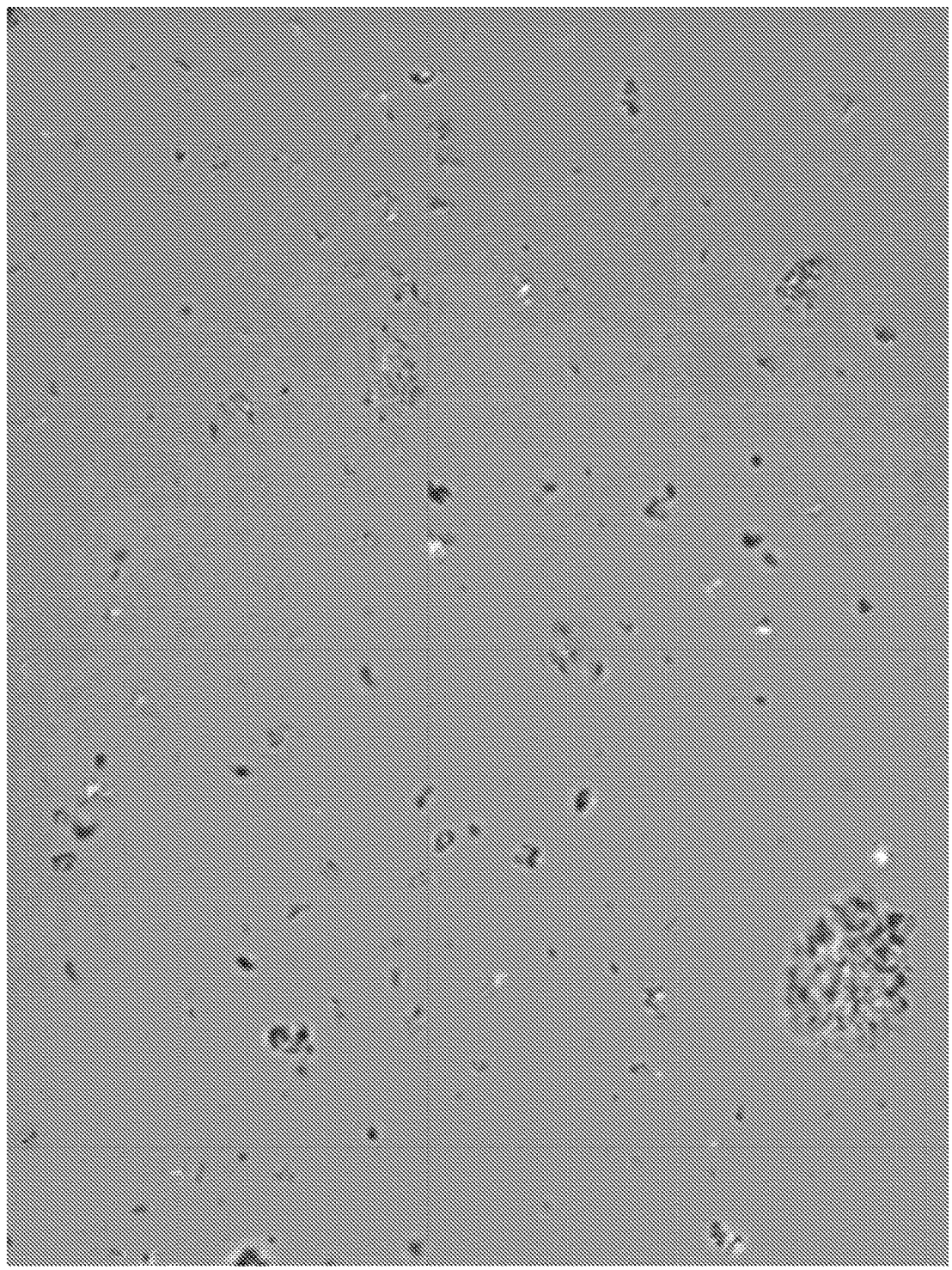
FIG. 1 depicts the polarized light microscopy for mostly amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, with some birefringent particles, generated from US Publication No. 2015/0011546.

When used alone, the terms "Form A", "Form B", and "Form C" refer to the crystalline polymorphic Forms A, B, and C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, respectively. The terms "Form A", "Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide", and "crystalline Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide" are used interchangeably. Similarly, "Form B", "Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide", and "crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide" are used interchangeably. Similarly, "Form C", "Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide", and "crystalline Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide" are used interchangeably.

It will be understood, that "Form A", "Form B", and "Form C" may include some water or solvent trapped within the lattice. Such forms are included herein provided they are substantially the same as the XRPD patterns/peaks described herein. Such forms are characterized e.g., by XRPD. As used herein, "anhydrous" means that the crystalline form comprises substantially no water in the crystal lattice e.g., less than 1% by weight as determined by Karl Fisher analysis.

The term "amorphous" means a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

As used herein, "(R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide" is intended to mean the following structure:

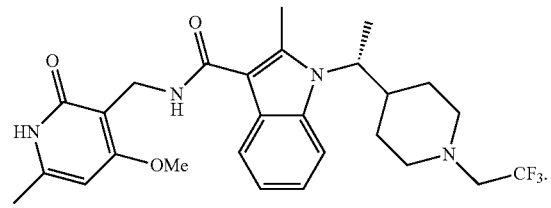 [SMILES: COc1cc(C)[nH]c(=O)c1CNC(=O)c1c(C)n([C@H](C)C2CCN(CC(F)(F)F)CC2)c2ccccc12]

The term "pharmaceutically acceptable carrier, adjuvant, or vehicle" refers to a non-toxic carrier, adjuvant, or vehicle that does not adversely affect the pharmacological activity of the compound with which it is formulated, and which is also safe for human use. Pharmaceutically acceptable carriers, adjuvants or vehicles that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, dicalcium phosphate, potassium hydrogen phosphate, sodium chloride, zinc salts, colloidal silica, magnesium trisilicate, polyvinyl pyrrolidone, polyvinylpyrrolidone-vinyl acetate, cellulose-based substances (e.g., microcrystalline cellulose, hydroxypropyl methylcellulose, hydroxypropyl methylcellulose acetate succinate, hydroxypropyl methylcellulose Phthalate), starch, lactose monohydrate, mannitol, sodium lauryl sulfate, and crosscarmellose sodium, polyethylene glycol, sodium carboxymethylcellulose, polyacrylates, polymethacrylate, waxes, polyethylene-polyoxypropylene-block polymers, polyethylene glycol and wool fat.

Description of Exemplary Compounds

In one aspect, the present disclosure provides crystalline Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, represented by the following structure:

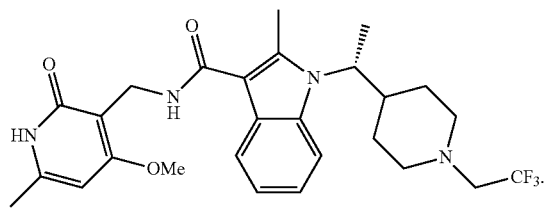 [SMILES: COc1cc(C)[nH]c(=O)c1CNC(=O)c1c(C)n([C@H](C)C2CCN(CC(F)(F)F)CC2)c2ccccc12]

In one aspect, crystalline Form A is characterized by at least three, at least four, at least five, or by at least six X-ray powder diffraction peaks at 2Θ angles selected from 8.52°, 16.82°, 19.10°, 19.48°, 20.62°, 23.78°, and 24.26°. Alternatively, crystalline Form A is characterized by major X-ray powder diffraction peaks at 2Θ angles at 8.52°, 16.82°, 19.10°, 19.48°, 20.62°, and 24.26°. In another alternative, crystalline Form A is characterized by X-ray powder diffraction peaks at 2Θ angles 8.52°, 16.82°, 19.10°, 19.48°, 20.62°, 23.78°, and 24.26°. In another alternative, crystalline Form A is characterized by X-ray powder diffraction peaks at 2Θ angles 8.52°, 12.38°, 14.18°, 14.42°, 16.82°, 19.10°, 19.48°, 20.62°, 22.14°, 23.78°, and 24.26°.

Figure 2:
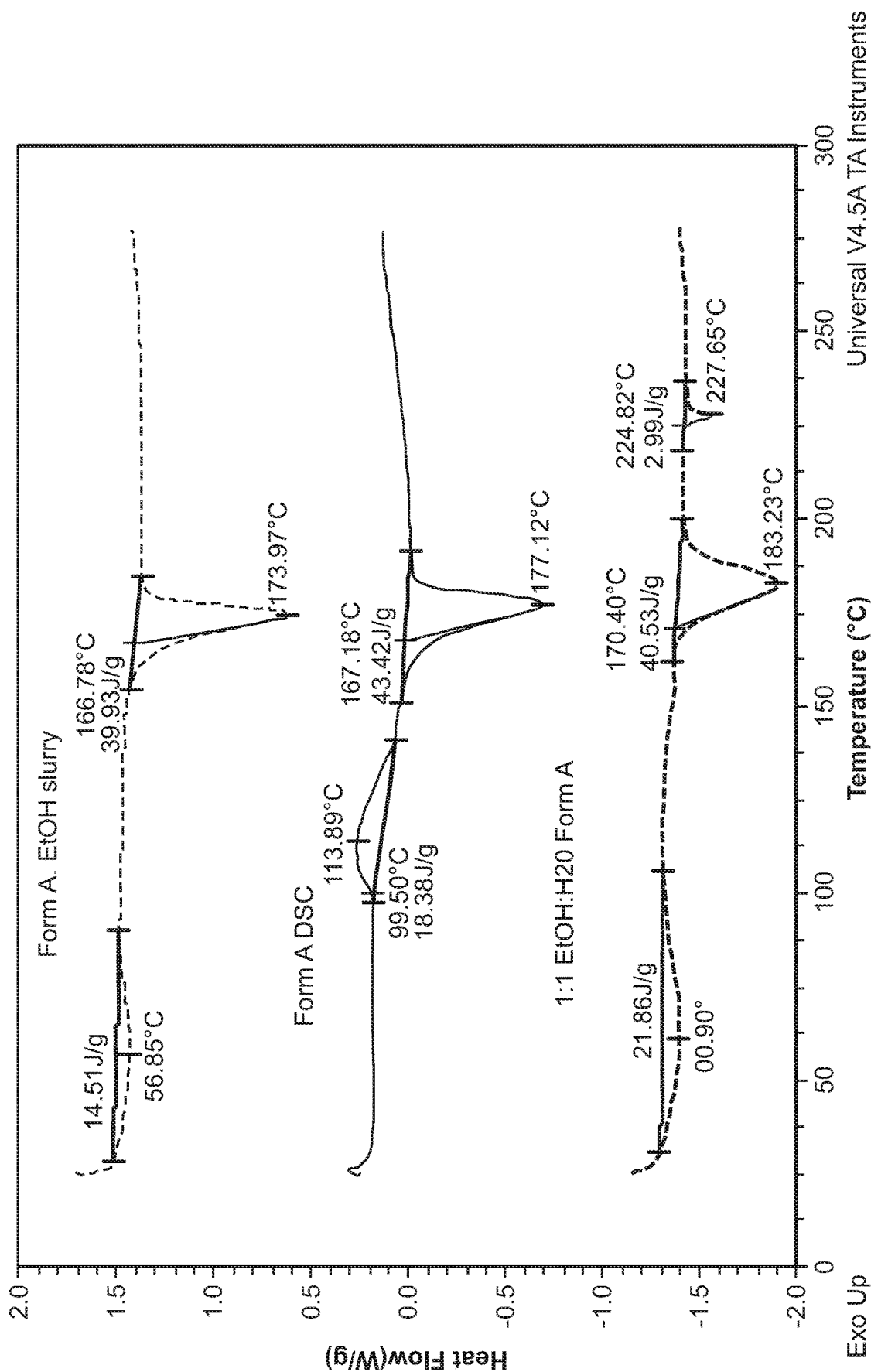
FIG. 2 illustrates exemplary DSC plots for Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide heated at 10° C./minute.

In one aspect, crystalline Form A is characterized by a DSC pattern that is substantially the same as FIG. 2.

Figure 3:
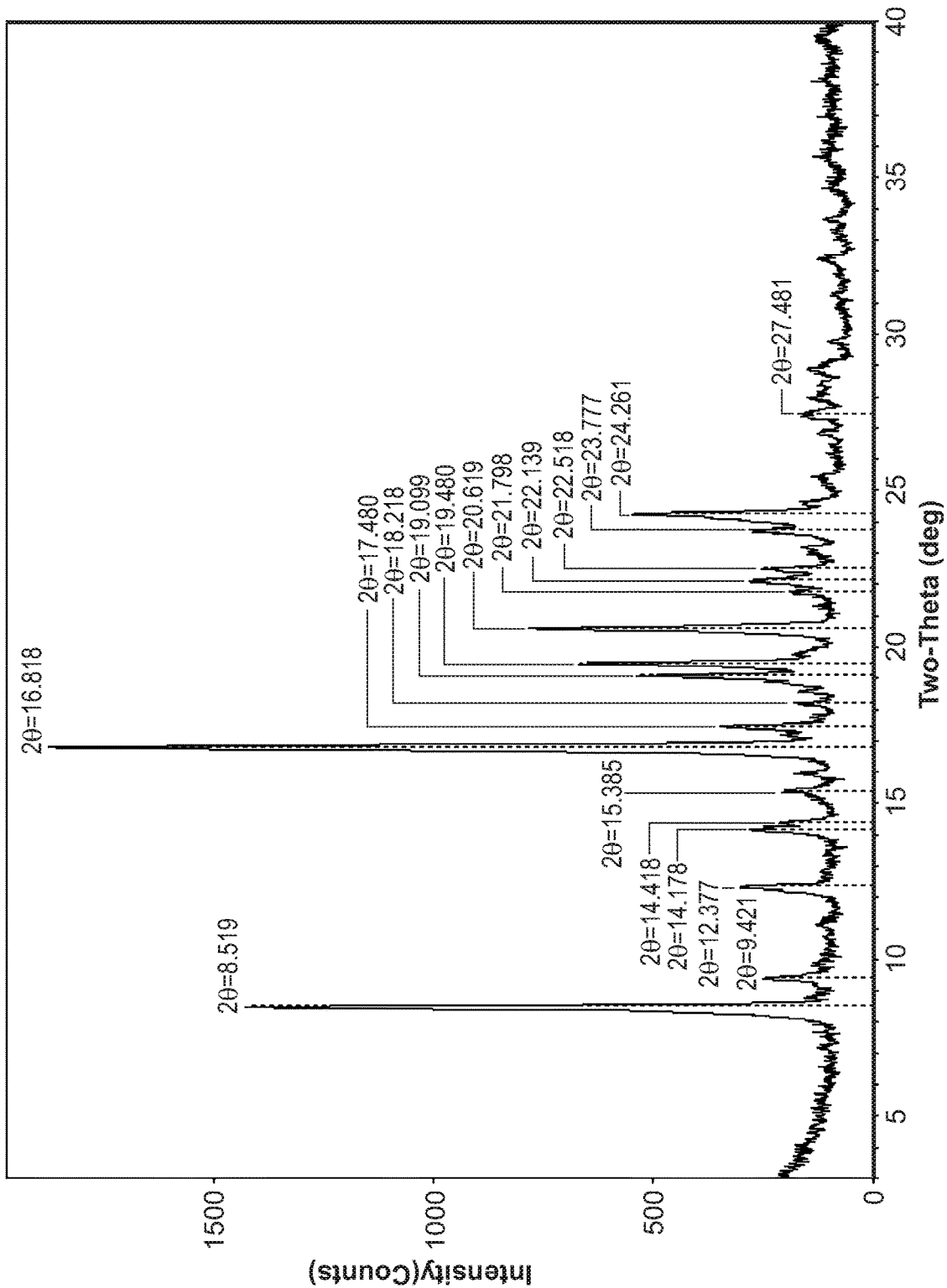
FIG. 3 depicts an X-ray powder diffraction pattern (XRPD) for crystalline Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, isolated from EtOH/$H_2O$.

In another aspect, crystalline Form A is characterized by an XRPD pattern that is substantially the same as FIG. 3.

Figure 4:
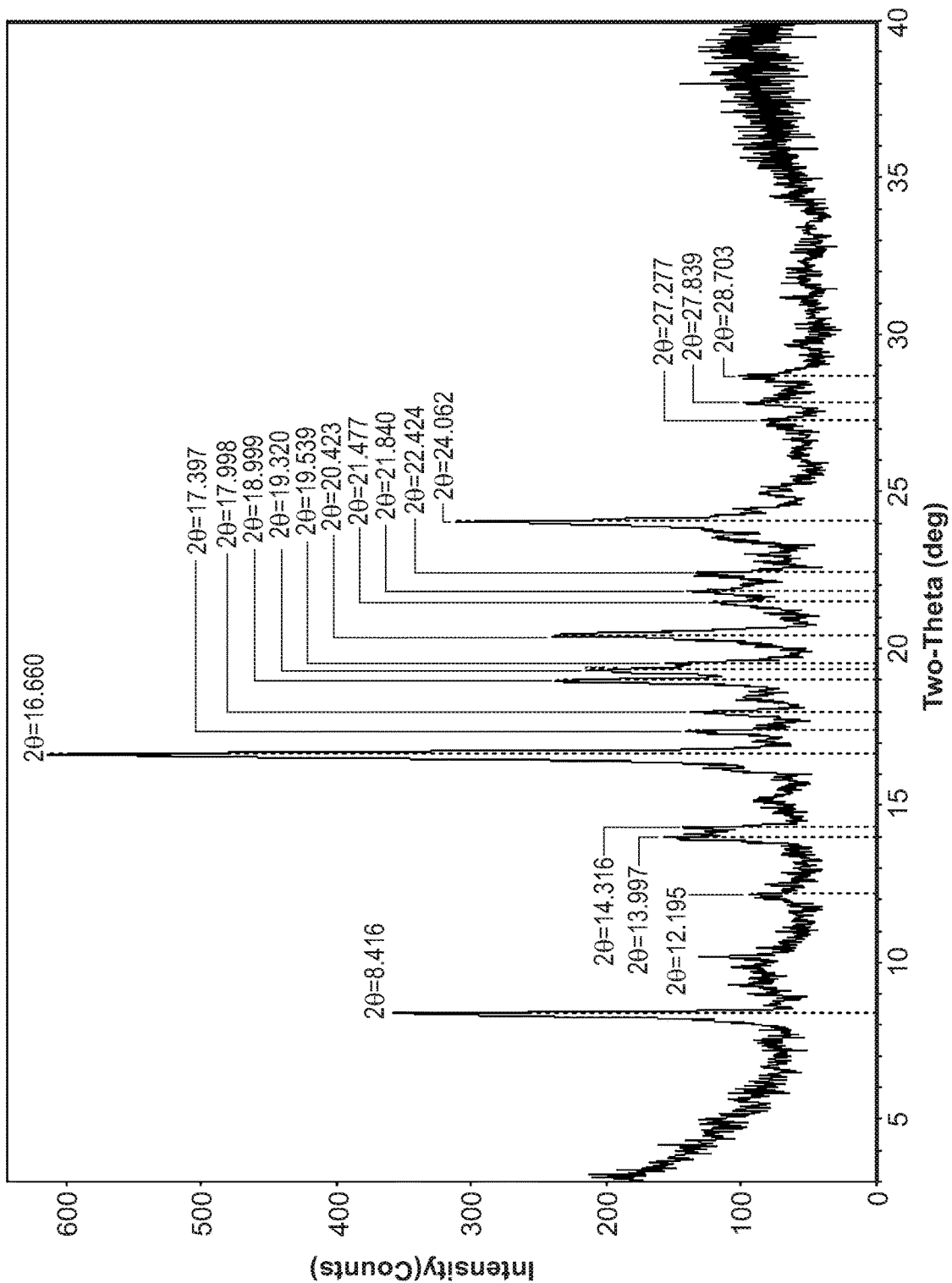
FIG. 4 depicts an X-ray powder diffraction pattern (XRPD) for crystalline Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, isolated from iPrOH/$H_2O$.

In another aspect, crystalline Form A is characterized by an XRPD pattern that is substantially the same as FIG. 4.

In another aspect, crystalline Form A is characterized by the peaks in Table 3.

In one aspect, the present disclosure provides crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, represented by the following structure:

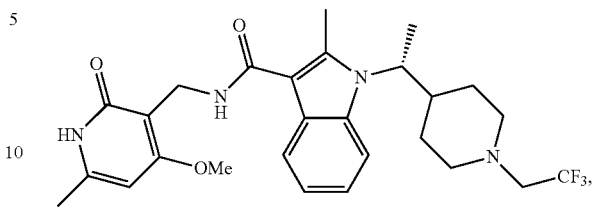

wherein crystalline Form B is at least 50% pure by weight, at least 75% pure by weight, at least 80% pure by weight, at least 90% pure by weight, at least 95% pure by weight, or at least 98% pure by weight.

In one aspect, crystalline Form B is characterized by at least three, at least four, at least five, at least six, or by at least seven X-ray powder diffraction peaks at 2Θ angles selected from 4.54°, 17.12°, 17.52°, 19.38°, 20.08°, 21.10°, 23.92°, and 25.2°. Alternatively, crystalline Form B is characterized by major X-ray powder diffraction peaks at 2Θ angles at 4.54°, 23.92°, and 25.2°. In another alternative, crystalline Form B is characterized by X-ray powder diffraction peaks at 2Θ angles 4.54°, 17.12°, 17.52°, 19.38°, 20.08°, 21.10°, 23.92°, and 25.2°. In another alternative, crystalline Form B is characterized by X-ray powder diffraction peaks at 2Θ angles 4.54°, 10.14°, 17.12°, 17.52°, 19.38°, 21.10°, 23.18°, 23.92°, 25.20°, 29.48°, and 35.18°.

Figure 6:
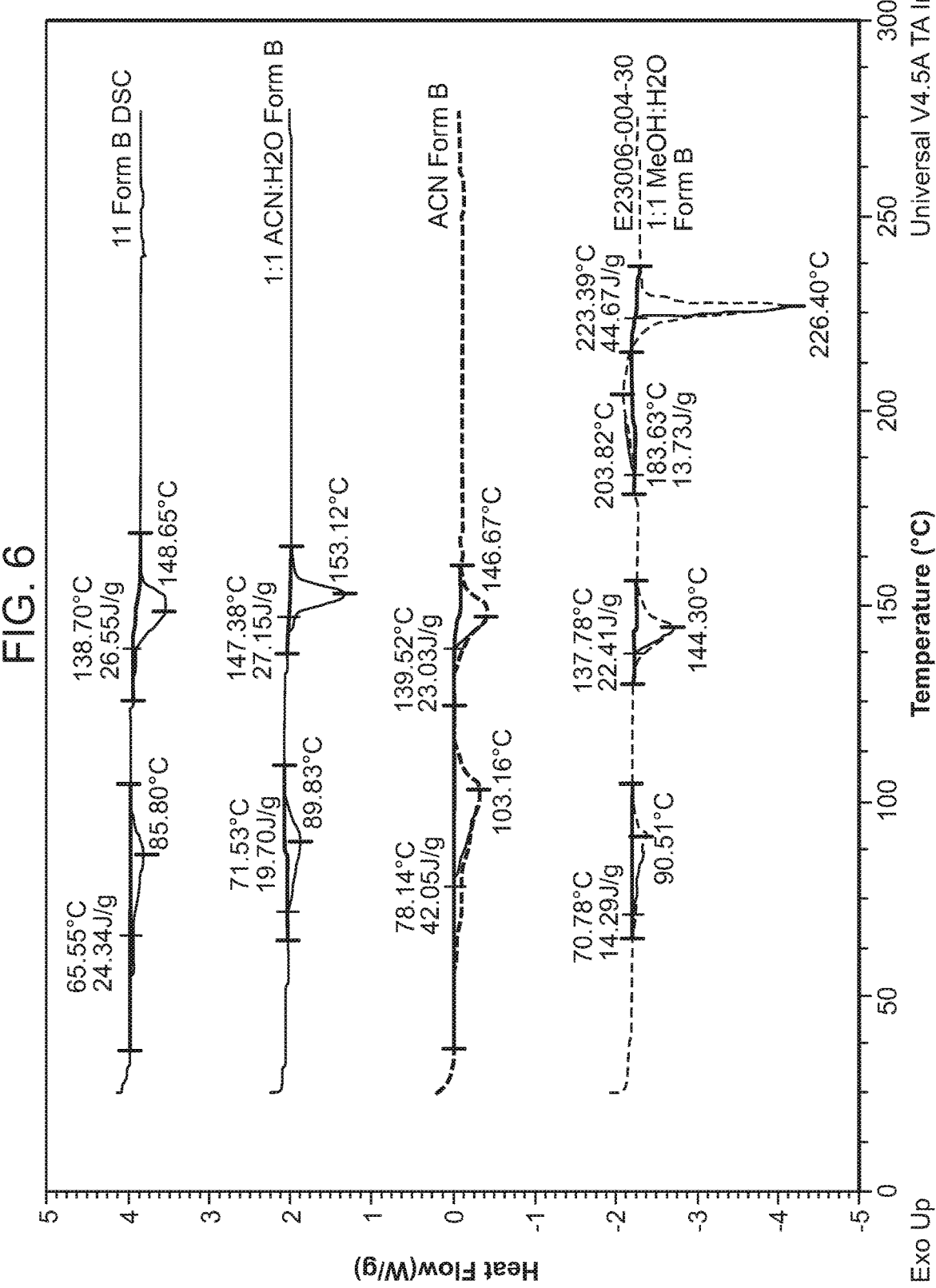
FIG. 6 illustrates exemplary DSC plots for Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide heated at 10° C./minute.

In one aspect, crystalline Form B is characterized by a DSC pattern that is substantially the same as FIG. 6.

Figure 7:
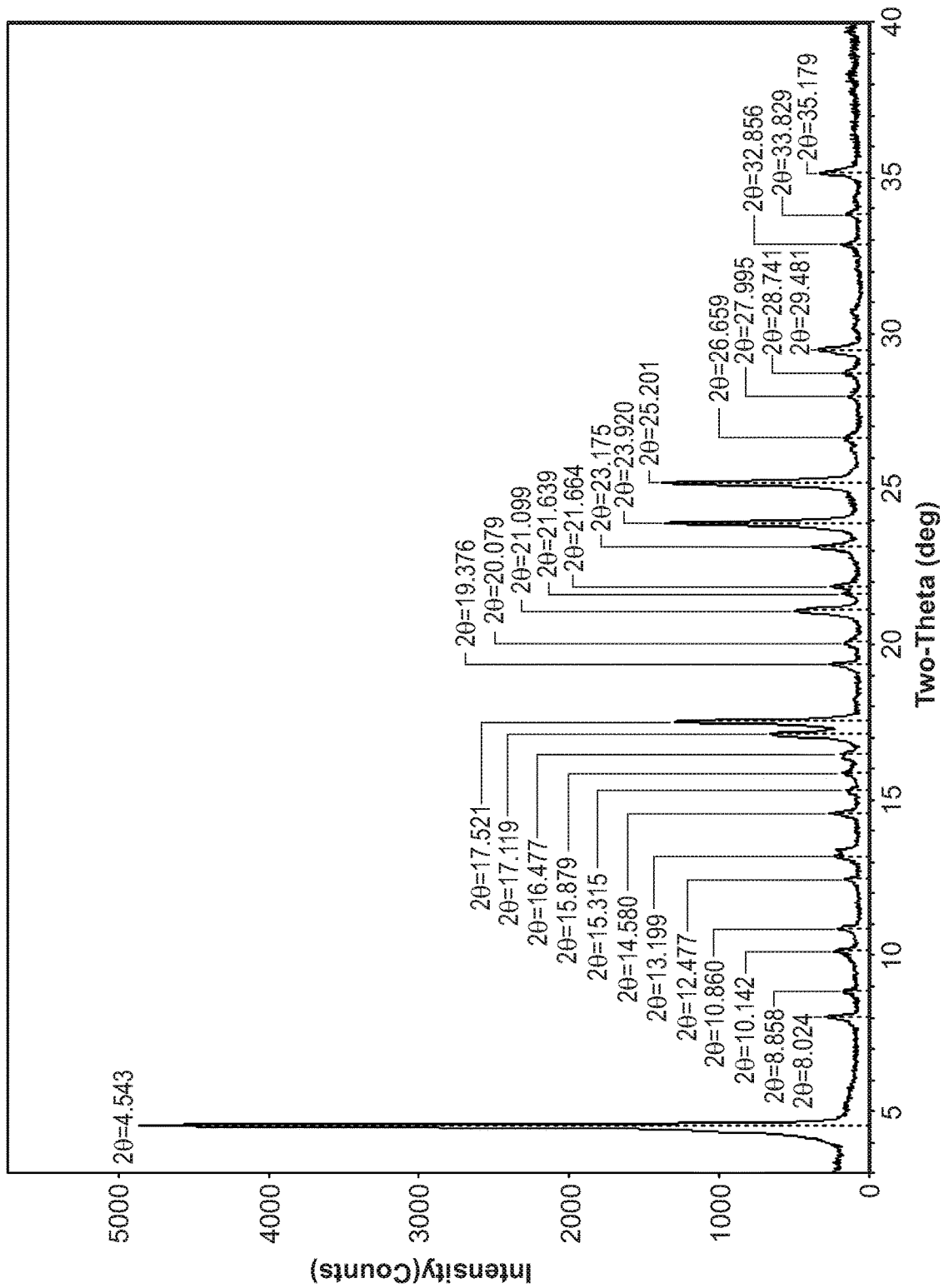
FIG. 7 depicts an X-ray powder diffraction pattern (XRPD) for crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, isolated from acetonitrile.

In another aspect, crystalline Form B is characterized by an XRPD pattern that is substantially the same as FIG. 7.

Figure 8:
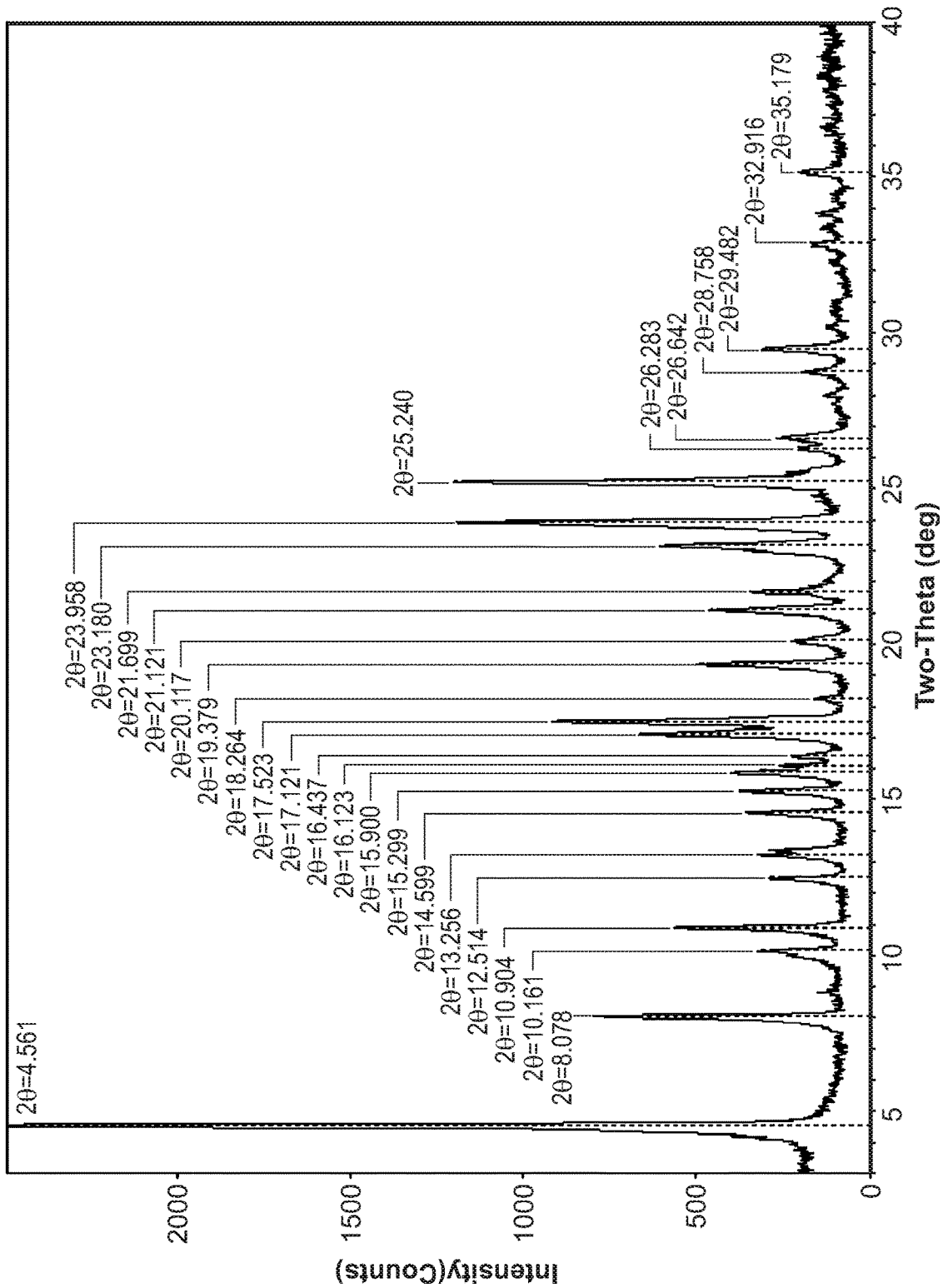
FIG. 8 depicts an X-ray powder diffraction pattern (XRPD) for crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, isolated from acetonitrile/$H_2O$.

In another aspect, crystalline Form B is characterized by an XRPD pattern that is substantially the same as FIG. 8.

Figure 9:
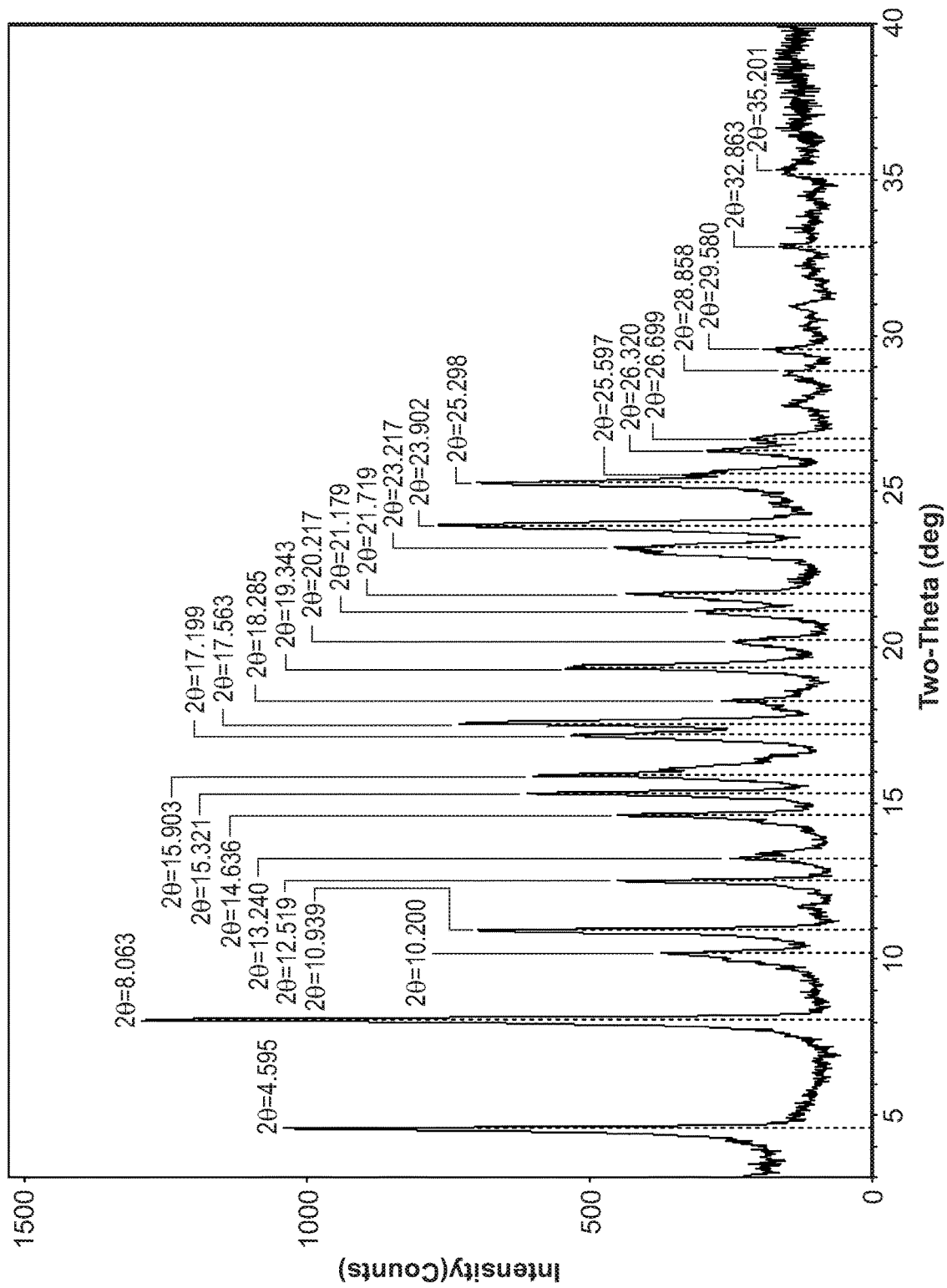
FIG. 9 depicts an X-ray powder diffraction pattern (XRPD) for crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, isolated from MeOH/$H_2O$.

In another aspect, crystalline Form B is characterized by an XRPD pattern that is substantially the same as FIG. 9.

In another aspect, crystalline Form B is characterized by the XRPD peaks in Table 4.

In one aspect, the present disclosure provides crystalline Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, represented by the following structure:

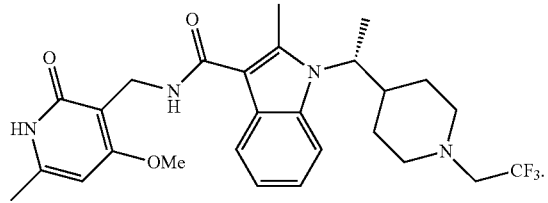 [SMILES: COc1cc(C)[nH]c(=O)c1CNC(=O)c1c(C)n([C@H](C)C2CCN(CC(F)(F)F)CC2)c2ccccc12]

In one aspect, crystalline Form C is characterized by at least three, at least four, at least five, at least six, or by at least seven X-ray powder diffraction peaks at 2Θ angles selected from 7.56°, 10.24°, 14.18°, 14.38°, 16.26°, 18.04°, 19.60°, and 21.52°. Alternatively, crystalline Form C is characterized by major X-ray powder diffraction peaks at 2Θ angles selected from 7.56°, 9.94°, 10.24°, 14.18°, 14.38°, 18.04°, 18.54°, 19.60°, 21.52°, 24.16°, and 24.46°. In another alternative, crystalline Form C is characterized by X-ray powder diffraction peaks at 2Θ angles 7.56°, 10.24°, 14.18°, 14.38°, 16.26°, 18.04°, 19.60°, and 21.52°. In another alternative, crystalline Form C is characterized by X-ray powder diffraction peaks at 2Θ angles 7.56°, 9.94°, 10.24°, 14.18°, 14.38°, 16.26°, 17.14°, 17.63°, 18.04°, 18.54°, 19.60°, 20.28°, 21.52°, 22.32°, 24.16°, 24.46°, 25.00°, and 27.88°.

Figure 10:
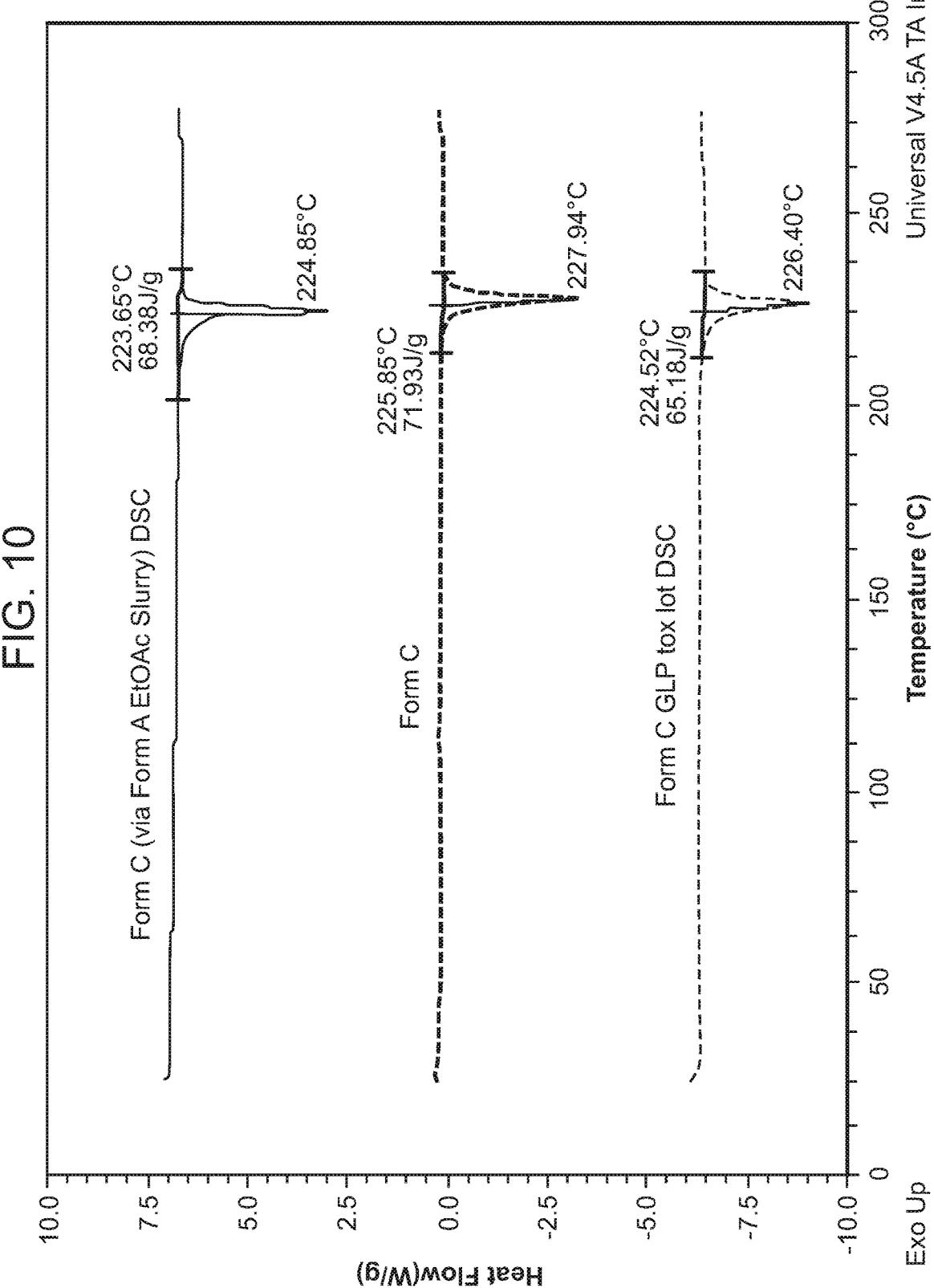
FIG. 10 illustrates exemplary DSC plots for Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide heated at 10° C./minute.

In one aspect, crystalline Form C is characterized by a DSC pattern that is substantially the same as FIG. 10.

Figure 11:
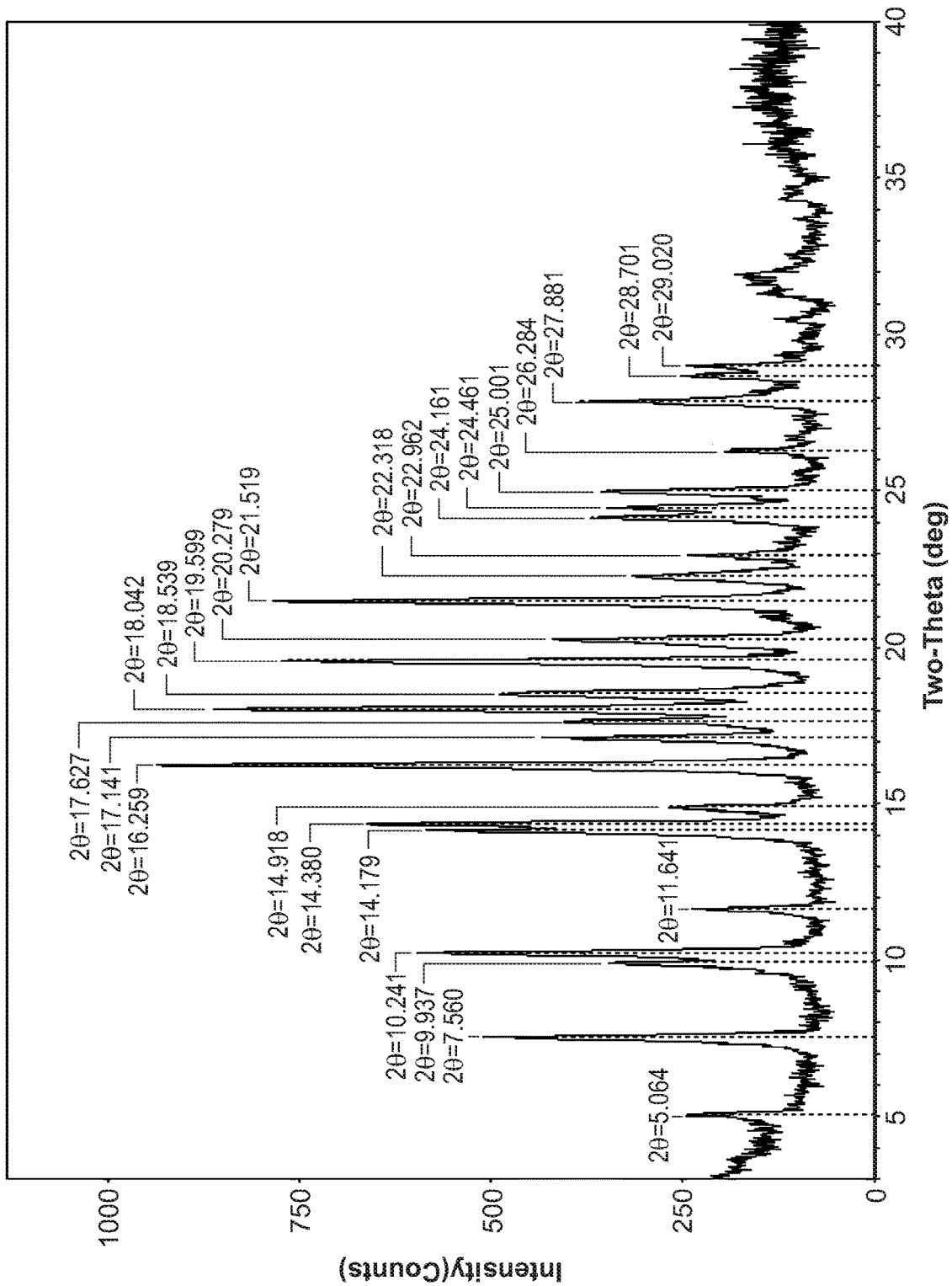
FIG. 11 depicts an X-ray powder diffraction pattern (XRPD) for crystalline Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, isolated from isopropyl acetate.

In another aspect, crystalline Form C is characterized by an XRPD pattern that is substantially the same as FIG. 11.

In another aspect, crystalline Form C is characterized by the XRPD peaks in Table 5.

Figure 5:
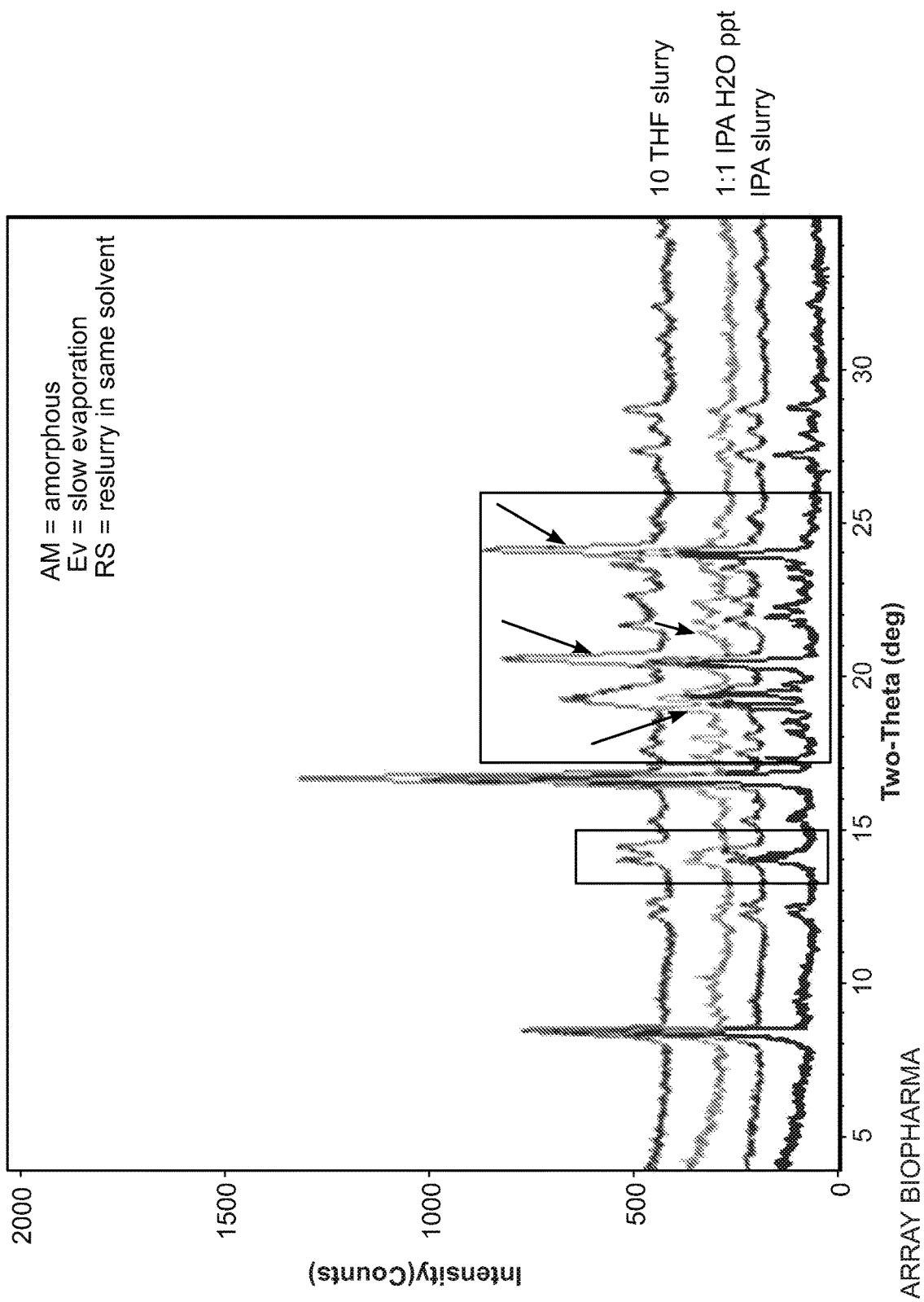
FIG. 5 illustrates subtle peak shifts represented by an overlay of X-ray powder diffraction patterns (XRPDs) for various samples of crystalline Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide.

It will be understood that the 2-theta values of the X-ray powder diffraction patterns for Form A, Form B, and Form C may vary slightly from one instrument to another and also depending on variations in sample preparation and batch to batch variation. Therefore, unless otherwise indicated, the XRPD patterns/assignments for the crystalline forms defined herein are not to be construed as absolute and can vary ±0.2 degrees. In the case of crystalline Form A, unless otherwise indicated, the XRPD patterns/assignments ranging from 13.5° to 14.50 and from 17.0° to 25.00 can vary by ±0.3 degrees. See e.g., FIG. 5. Without wishing to be bound by theory, it is believed that this additional variation may be indicative of some level of solvent trapped within the lattice.

As intended herein, "substantially the same XRPD pattern as shown in FIG. 3" means that for comparison purposes, the XRPD has at least 90% of the peaks shown in FIG. 3. This applies similarly to FIGS. 3-5, 7-9, and 11. It is to be further understood that for comparison purposes, some variability in 2Θ angles from those shown in FIGS. 3-5, 7-9, and 11 are allowed, such as ±0.2 degrees, except for the 2Θ angles ranging from 13.5° to 14.50 and from 17.0° to 25.00 in the case of Form A (FIGS. 3-5, which can vary by ±0.3 degrees.

In one aspect, the present disclosure provides a process for preparing crystalline Form A of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide. Such a process includes, e.g., preparing a slurry of amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide in e.g., neat ethanol (200 proof); mixture of ethanol in water, heptane, or methyl tert-butyl ether; dichloromethane; and isopropanol/water (50:50). Form A can also be prepared by seeding with Form A, a suspension (slurry) of Form B or Form C in ethanol/water (50:50).

In one aspect, the present disclosure provides a process for preparing crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide. Such a process includes, e.g., preparing a slurry of amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide in e.g., methanol, acetonitrile, methanol/water (50:50), acetonitrile/water (50:50), and methanol/methyl tert-buthyl ether. Form B can also be prepared by seeding with Form B, a suspension (slurry) of Form A or Form C in acetonitrile.

In one aspect, the present disclosure provides a process for preparing crystalline Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide. Such a process includes, e.g., agitating a mixture comprising amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide and isopropyl acetate (iPrOAc) at e.g., a temperature of about 65° C.

Crystalline Form C can also be obtained by preparing a concentrated solution of amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide at or near the reflux temperature of an organic solvent or solvent system; and allowing the solution to cool to ambient temperature or preparing a slurry of amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide.

Exemplary organic solvents and solvent systems for this processes include e.g., ethanol (200 proof), 2-methoxyethanol, 2-propanol, n-propanol, butanol, methyl ethyl glycol, methyl acetate, ethyl acetate, isopropyl acetate, 1,2-dichloromethane, chloroform, dimethoxyethane, dimethyl sulfoxide, N-methyl 2-pyrrolidone, acetone, methyl ethyl ketone, methyl isobutyl ketone, tetrahydrofuran, 1,4-dioxane vapor diffusion, methyl t-butyl ether, toluene, benzene vapor diffusion, and xylenes. Form C can also be prepared by seeding with Form C a slurry of Form A or Form B in isopropyl acetate.

Processess for preparing each of the crystalline Forms A, B, and C also include cooling down saturated solutions with or without seeding solutions of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide. Solvent systems that are appropriate in the above slurries are also compatible with cooling down saturated solutions with or without seeding.

Uses, Formulation and Administration

Pharmaceutically Acceptable Compositions

According to other aspects, the present disclosure relates to a method of modulating a histone modifying enzyme using a composition comprising Form A, Form B, or Form C and a pharmaceutically acceptable carrier, adjuvant, or vehicle. The amount of crystalline form is a provided composition is such that is effective to measurably modulate a histone methyl modifying enzyme, or a mutant thereof, in a biological sample or in a patient. In certain embodiments, the amount of crystalline form in a provided composition is such that it is effective to measurably modulate a histone methyl modifying enzyme, or a mutant thereof, in a biological sample or in a patient.

In one aspect, pharmaceutical compositions described herein comprise least 50% by weight, at least 70% by weight, at least 80% by weight, at least 90% by weight, at least 95% by weight, or at least 99% by weight of crystalline Form A, crystalline Form B, or crystalline Form C; and a pharmaceutically acceptable carrier or diluent.

According to other aspects, the present disclosure relates to a method of inhibiting EZH2 using a composition comprising the crystalline forms described herein and a pharmaceutically acceptable carrier, adjuvant, or vehicle. The amount of the crystalline form in a provided composition is such that is effective to measurably inhibit EZH2, or a mutant thereof, in a biological sample or in a patient. In certain aspects, a provided composition is formulated for administration to a patient in need of such composition. In some aspects, a provided composition is formulated for oral administration to a patient.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Other forms of administration are as described in U.S. Patent Publication No. 2012/0157428. Dosage forms for oral administration are also as described in U.S. Patent Publication No. 2015/0011546, the contents of which are incorporated herein by reference.

The amount of provided crystalline form that may be combined with carrier materials to produce a composition in a single dosage form will vary depending upon the patient to be treated and the particular mode of administration. Provided compositions may be formulated such that a dosage of between 0.001-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided crystalline form in the composition will also depend upon the particular compound in the composition.

Uses of Compounds and Pharmaceutically Acceptable Compositions

The crystalline forms described herein and compositions thereof are generally useful for modulating the activity of one or more enzymes involved in epigenetic regulation, such as EZH2 and others described in e.g., U.S. Patent Publication No. 2015/0011546. Thus, in some aspects, the present disclosure provides a method of inhibiting one or more enzymes involved in epigenetic regulation, such as EZH2, by administering a provided crystalline form or composition.

The present disclosure also relates to treating diseases and/or disorders associated with overexpression of EZH1 or EZH2 and/or expression of a mutant form of EZH2, particularly those mutant forms that alter EZH2 substrate activity (e.g., as those described in U.S. Patent Publication No. 2015/0011546), with a crystalline form or composition thereof described herein. The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). In some embodiments, crystalline forms and compositons thereof are useful in treating diseases and/or disorders associated with the presence of EZH2 having a Y641N, Y641C, Y641F, Y641H, Y641S, A677G, or A687 mutation. In one aspect, the EZH2 has a Y641N mutation.

As used herein, the terms "treatment," "treat," and "treating" refer to reversing, alleviating, or inhibiting the progress of a disease or disorder, or one or more symptoms thereof, as described herein.

Diseases and conditions treatable according to the methods described herein include, but are not limited to, diseases and/or disorders associated with cellular proliferation. In some embodiments, the crystalline forms and compositions thereof described herein are useful in treating diseases and/or disorders associated with misregulation of cell cycle or DNA repair. In some embodiments, the crystalline forms and compositions thereof described herein are useful in treating cancer. Exemplary types of cancer include e.g., adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one aspect, the cancer treated by the crystalline forms and compositions thereof described herein is selected from breast cancer, prostate cancer, colon cancer, renal cell carcinoma, glioblastoma multiforme cancer, bladder cancer, melanoma, bronchial cancer, lymphoma, liver cancer, multiple myeloma, lymphoma, ovarian cancer, NSCL, pancreatic cancers, malignant rhabdoid tumor, synovial sarcoma, and glioma.

Another aspect of the present disclosure is the use of one or more of the crystalline forms as described herein in the manufacture of a medicament for use in the treatment of a disorder or disease herein. Another object of the present disclosure is one or more of the crystalline forms or composition described herein for use in the treatment of a disorder or disease herein.

EXEMPLIFICATION

As depicted in the Examples below, in certain exemplary embodiments, crystalline Forms A, B, and C are prepared according to the following general procedures.

XRPD analyses were conducted using a Rigaku Ultima III X-Ray diffractometer operating with a Cu radiation source at 45 kV, 40 mA through a Ni filter with a divergence slit of ⅔°, Divergence H.L. slit of 10 mm, scatter slit set to "Auto", and receiving slit of 0.3 mm. Samples were placed on Si zero-return sample holders and analysis was performed using continuous scan from 3° to 400 2θ at 2°/min with a step size of 0.02°/second and a step time of 0.6 point/second. Samples were rotated plane parallel to sample surface at 60 rpm. Peak assignments were performed using Jade 7 software.

Differential Scanning Calorimetry was performed on a TA Instruments DSC Q1000 on the sample "as is." Sample were weighed into an aluminum pan, covered with a pierced lid, and then crimped and analyzed from −25 to 280° C. ramped at 10° C./min.

For TGA, weight loss was monitored as a function of temperature using a TA Instruments TGA Q50. Samples were run from 25° C. to 300° C. or >20% decomposition at a heating rate of 10° C./min in open platinum TGA pans under an inert nitrogen atmosphere. Weight losses were calculated from the highest point in the baseline to the point at which the onset of melt occurred or to the visible plateau before the onset of decomposition.

Moisture sorption profiles were generated isothermally at 25° C. using a Hiden IGAsorp moisture sorption analyzer. Samples were dried on the instrument under inert nitrogen at 40° C. for 60 min. Following drying the samples moisture sorption was determined by performing one full cycle of weight measurements at 0, 10, 20, 30, 40, 50, 60, 70, 80, 90 and 95% RH, with exposure time at each humidity set point dependent upon a minimum of 99% confidence in the F1 fit model or 15 min, with a maximum timeout of 120 min. The moisture sorption isotherms were plotted as a function of weight change (relative weight % of the dried starting weight) and % RH.

Figure 12:
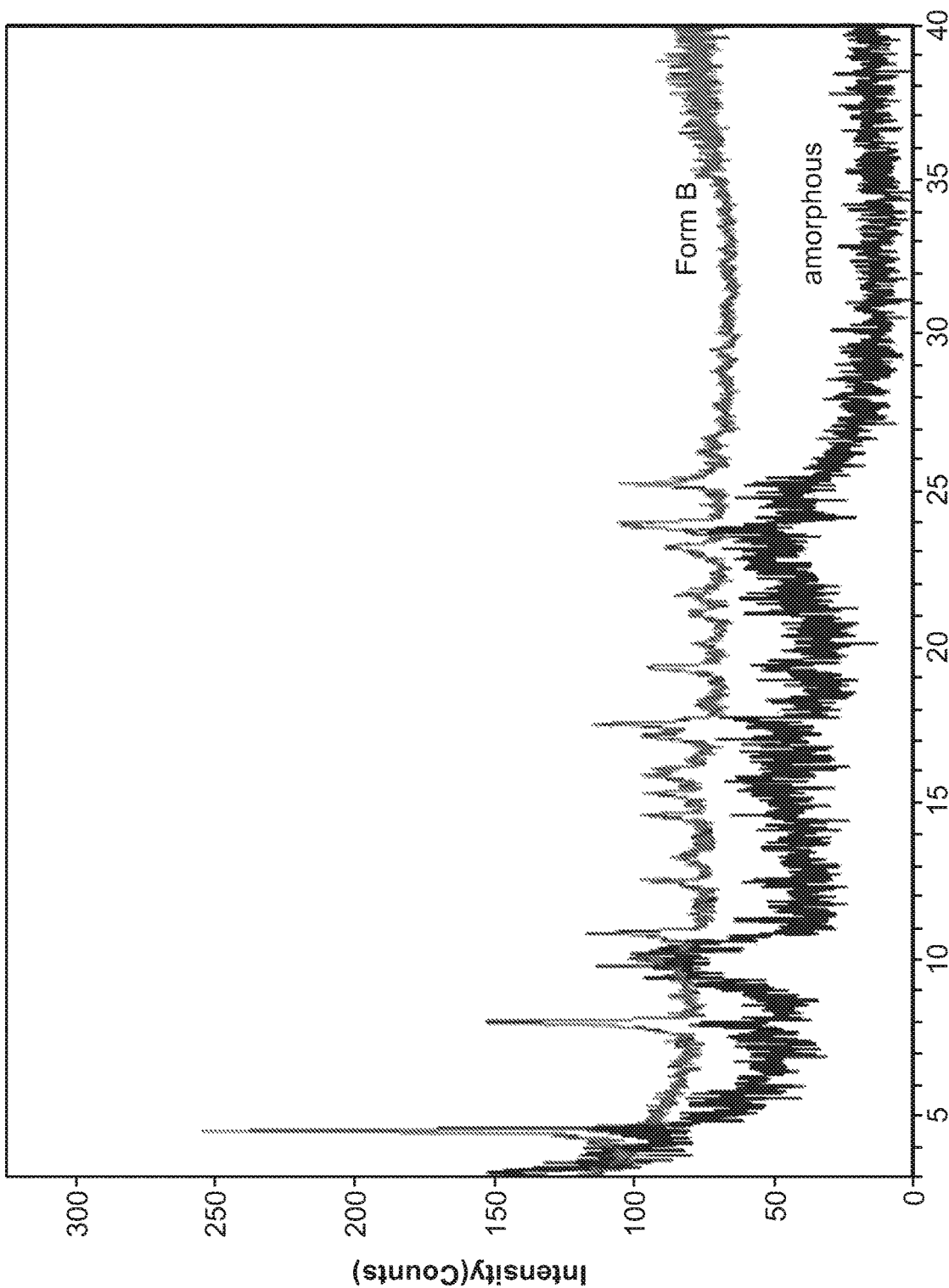
FIG. 12 depicts an overlay X-ray powder diffraction pattern (XRPD) between crystalline Form B of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide and mostly amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide generated from US Publication No. 2015/0011546.

The material obtained for (R)—N-((4-methoxy-6-methyl-2-oxo-1,2-dihydropyridin-3-yl)methyl)-2-methyl-1-(1-(2,2,2-trifluoroethyl)piperidin-4-yl)ethyl)-1H-indole-3-carboxamide, following the methods described in Example 28, compound 365 of U.S. Patent Publication No. 2015/0011546 produces mostly amorphous material with very weak XRPD signal having some similarity to Form B. The microscopy results of this material is shown in FIG. 1 and the XRPD overlay with Form B is shown in FIG. 12.

Example 1: Preparation of Monohydrate Crystalline Form A, B, and C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide

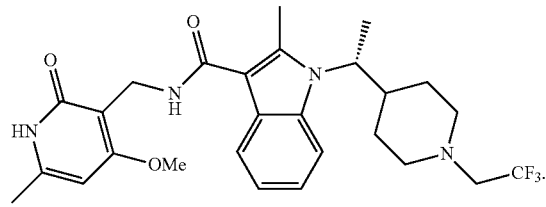 [SMILES: COc1cc(C)[nH]c(=O)c1CNC(=O)c1c(C)n([C@H](C)C2CCN(CC(F)(F)F)CC2)c2ccccc12]

Polymorph screen samples were prepared by initially in 33 solvent systems with 29 neat solvents and 4 combinations of 1:1 solvent:water. Polymorph screen samples were prepared with amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide by aliquoting from a stock solution of amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide in dichloromethane and evaporating to dryness. Samples that did not generate solids as a saturated solution at ambient conditions were slowly evaporated to dryness. Dry samples that did not yield crystalline solids were reconstituted in the original solvent and subject to vapor diffusion at ambient temperature with MBTE as an antisolvent. Dry sample that yield trace crystalline solids were re-slurried in a few drops of the original solvent to break up the solids and promote additional crystal growth. Vapor diffusion samples yielding mostly amorphous solids were also re-slurried in the original solvent to generate crystalline material.

Resulting solids were isolated by spatula or centrifugation and screened for birefringence using polarized light microscopy. The resulting form was determined by XRPD analysis of the wet cake for all birefringent solids. DSC and TGA analysis after vacuum drying at 40° C. for at least 4 hours was performed in isolated instances to spot check and build data for each form. Table 1 details the results.

TABLE I

| Solvent Abbreviation | Solvent Name | Resulting Form |
|---|---|---|
| H$_2$O | Water | N/A |
| MeOH | Methanol | B |
| EtOH | Ethanol (200 proof) | A$^{RS}$ |
| 2-MetOH | 2-Methoxyethanol | C$^{RS}$ |

TABLE I-continued

| Solvent Abbreviation | Solvent Name | Resulting Form |
|---|---|---|
| IPA | 2-propanol | C |
| n-PrOH | n-propanol | C |
| BuOH | Butanol | C |
| MEG | Methyl ethyl glycol | $C^{EV}$ |
| MOAc | Methyl acetate | C |
| EtOAc | Ethyl acetate | C |
| IPAC | Isopropyl acetate | C |
| ACN | Acetonitrile | B |
| DCM | Dichloromethane | $A^{RS}$ |
| DCE | Dimethoxyethane | C |
| CHCl$_3$ | Chloroform | C |
| DME | Dimethoxyethane | C |
| DMSO | Dimethyl sulfoxide | $C^{EV}$ |
| NMP | N-methyl 2-pyrrolidone | $C^{RS}$ |
| ACE | Acetone | $C^{RS}$ |
| MEK | Methyl ethyl ketone | $C^{RS}$ |
| MIBK | Methyl isobutyl ketone | C |
| THF | Tetrahydrofuran | $C^{VD-RS}$ |
| DIOX/MTBE | 1,4-Dioxane vapor diffusion | $C^{VD}$ |
| MTBE | Methyl t-butyl ether | C |
| HEP | Heptane | $N/A^{EV}$ |
| TOL | Toluene | $C^{VD}$ |
| Benz/MTBE | Benzene vapor diffusion | $C^{VD-RS}$ |
| Xyl | Xylenes | C |
| TFE | Trifluoroethanol | N/A |
| MeOH/H$_2$O 50:50 | Methanol/water 50:50 | B |
| EtOH/H$_2$O 50:50 | Ethanol/water 50:50 | A |
| ACN/H$_2$O 50:50 | Acetonitrile/water 50:50 | B |
| IPA/H$_2$O 50:50 | Isopropanol/water 50:50 | A |

EV = slow evaporation
VD = vapor diffusion
RS = reslurry
N/A = data not available Table 2 compares certain physical characteristics of Form A, Form B, and Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide.

TABLE 2

| | Form A | Form B | Form C | Amorphous |
|---|---|---|---|---|
| DSC | Melt max ~173-183° C. | Melt/recryst ~80-105° C. and melt at ~145-155° C. | Melt max ~225-228° C. | Tg midpoint ~80-115° C. |
| TGA | 1.5-5% wt loss before onset of melt | ~0-2.5 wt loss before onset of first melt | ~1% wt loss before onset of melt | ~5% wt loss before decomposition |
| DVS | 2% wt gain at 80% RH, 5.3 wt gain at 95% RH, some hysteresis. Final sample wt ~0.8 lower than starting wt | 7.2% wt gain at 95% RH | Non-hygroscopic ≤ 2.3% wt gain at 95% RH | 7.4% wt gain at 95% RH, some hysteresis. Final same wt ~1% lower than starting wt. |
| Post DVS | 1% reduction in wt loss by TGA. No other changes | No significant changes by PLM XRD, DSC, TGA | No significant changes by PLM XRD, DSC, TGA | Amorphous |
| Aqueous Solubility | pH 1.2: ≥961 ug/mL pH 6.5: 31 ug/mL pH 7.4: 28 ug/mL | pH 1.2: ≥970 ug/mL pH 6.5: 120 ug/mL pH 7.4: 112 ug/mL | pH 1.2: ≥913 ug/mL pH 6.5: 14 ug/mL pH 7.4: 9 ug/mL | pH 1.2: ≥921 ug/mL pH 6.5: 18 ug/mL pH 7.4: 140 ug/mL |

A representative listing of XRPD peaks for each of Form A, Form B, and Form C of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide are provided in Tables 3-5.

TABLE 3

Form A

| 2-Theta | Height | Rel. Peak Height [%] | Rel. Area [%] |
|---|---|---|---|
| 8.519 | 1320 | 74.6 | 65.5 |
| 9.421 | 143 | 8.1 | 8.1 |
| 12.377 | 210 | 11.9 | 14 |
| 14.178 | 189 | 10.7 | 14.8 |
| 14.418 | 116 | 6.6 | 10.1 |
| 15.385 | 108 | 6.1 | 6.3 |
| 16.818 | 1769 | 100 | 100 |
| 17.48 | 196 | 11.1 | 5.5 |
| 18.218 | 81 | 4.6 | 2.2 |
| 19.099 | 433 | 24.5 | 30.3 |
| 19.48 | 566 | 32 | 37.3 |
| 20.619 | 680 | 38.5 | 33.8 |
| 21.798 | 89 | 5 | 5.6 |
| 22.139 | 176 | 9.9 | 13.6 |
| 22.518 | 145 | 8.2 | 8.2 |
| 23.777 | 177 | 10 | 16 |
| 24.261 | 450 | 25.4 | 36.9 |
| 27.481 | 85 | 4.8 | 5.2 |

TABLE 4

Form B

| 2-Theta | Height | Rel. Peak Height [%] | Rel. Area [%] |
|---|---|---|---|
| 4.543 | 4698 | 100 | 100 |
| 8.024 | 214 | 4.6 | 4.7 |
| 8.858 | 93 | 2 | 1.6 |
| 10.142 | 158 | 3.4 | 5.6 |
| 10.86 | 131 | 2.8 | 2.9 |
| 12.477 | 92 | 2 | 2.1 |
| 13.199 | 159 | 3.4 | 6 |
| 14.58 | 193 | 4.1 | 3.7 |
| 15.315 | 61 | 1.3 | 1.1 |
| 15.879 | 90 | 1.9 | 2.6 |
| 16.477 | 96 | 2 | 3.2 |
| 17.119 | 569 | 12.1 | 17.9 |
| 17.521 | 1211 | 25.8 | 29 |
| 19.376 | 200 | 4.3 | 5.1 |
| 20.079 | 89 | 1.9 | 2.6 |
| 21.099 | 420 | 8.9 | 12.1 |
| 21.639 | 107 | 2.3 | 3.5 |
| 21.864 | 175 | 3.7 | 4.9 |
| 23.175 | 274 | 5.8 | 6.9 |
| 23.92 | 1260 | 26.8 | 28.1 |
| 25.201 | 1290 | 27.5 | 32.7 |
| 26.659 | 100 | 2.1 | 3.9 |
| 27.995 | 66 | 1.4 | 1.7 |
| 28.741 | 106 | 2.3 | 3 |
| 29.481 | 264 | 5.6 | 7.2 |
| 32.856 | 116 | 2.5 | 3.2 |
| 33.823 | 78 | 1.7 | 1.8 |
| 35.179 | 250 | 5.3 | 6.7 |

TABLE 5

Form C

| 2-Theta | Height | Rel. Peak Height [%] | A % |
|---|---|---|---|
| 5.064 | 125 | 14.9 | 8.6 |
| 7.56 | 434 | 51.7 | 43.4 |

TABLE 5-continued

Form C

| 2-Theta | Height | Rel. Peak Height [%] | A % |
|---|---|---|---|
| 9.937 | 263 | 31.3 | 41.7 |
| 10.241 | 514 | 61.2 | 59.6 |
| 11.641 | 163 | 19.4 | 11.8 |
| 14.179 | 505 | 60.1 | 94.5 |
| 14.38 | 581 | 69.2 | 100 |
| 14.918 | 154 | 18.3 | 11 |
| 16.259 | 840 | 100 | 76.1 |
| 17.141 | 302 | 36 | 22.7 |
| 17.627 | 245 | 29.1 | 20.3 |
| 18.042 | 737 | 87.8 | 68.9 |
| 18.539 | 391 | 46.6 | 45.3 |
| 19.599 | 674 | 80.3 | 63.1 |
| 20.279 | 312 | 37.2 | 32 |
| 21.519 | 683 | 81.3 | 70.3 |
| 22.318 | 209 | 24.9 | 24.7 |
| 22.962 | 143 | 17 | 12.4 |
| 24.161 | 270 | 32.2 | 32.5 |
| 24.461 | 256 | 30.5 | 41.5 |
| 25.001 | 241 | 28.7 | 17.9 |
| 26.284 | 111 | 13.2 | 9.6 |
| 27.881 | 285 | 34 | 23.8 |
| 28.701 | 135 | 16.1 | 15.8 |
| 29.02 | 140 | 16.7 | 15.3 |

A scale up of crystalline Form C was performed as follows.

A 100 L round bottom reactor was charged with CDI (1.14 kg, 7.0 mol). The reactor was equipped with mechanical stirring, and static $N_2$. Tetrahydrofuran was charged (10.8 L, 5 L/kg) and the suspension was heated to 58° C. In a separate vessel, (R)-2-methyl-1-(1-(1-(2,2,2-trifluoroethyl)piperidin-4-yl)ethyl)-1H-indole-3-carboxylic acid (2.15 kg) was dissolved in tetrahydrofuran (8.6 L, 4 L/kg). The solution was added to the CDI mixture via addition funnel at a rate such that the $CO_2$ off-gassing was controlled and the reaction temperature was maintained at <60° C. (~1 hour). The reaction was agitated at 60° C. until conversion to the acyl-imidazole was complete by HPLC (<1%). 2-Propanol (895 mL, 11.7 mol) was charged and the resulting mixture was stirred at 60° C. for 15 min. Charged 3-(aminomethyl)-4-methoxy-6-methylpyridin-2(1H)-one (1.252 kg, 7.0 mol) to the reactor and agitated at 60° C. overnight until >96% conversion of the acyl-imidazole was observed by HPLC. The reaction was cooled to room temperature and transferred to a separatory funnel, where it was further diluted with iPrOAc (54 L, ~25 L/kg). The reaction stream was washed with water (10.8 L, 5 L/kg) two times. The resulting product-rich iPrOAc layer was polish filtered and concentrated to a target volume of (~2 L/kg based on input).

A second reaction was run on 2.17 kg scale under reaction conditions identical to those described above. After the aqueous workup and polish filtration operations were completed for the second reaction, it was combined with the first reaction (see paragraph above) in a 100 L round bottom reactor for further distillation and product isolation. The combined mixture was distilled to a target volume of 2 L/kg (based on the combined input) and was then diluted with iPrOAc (34.5 L, 8 L/kg) resulting in a final concentration of ~10 L/kg. The mixture was then heated to 65° C. and agitated overnight to achieve conversion to Form C. Note— During the form conversion, the initial solution is pale yellow, and subsequent crystallization results in a thick slurry that gradually becomes less viscous. The slurry was subsequently cooled to 25° C. and agitated at room temperature (<30° C.) overnight. The product was collected by vacuum filtration, and the flask and filter cake were rinsed with iPrOAc (4 L/kg total in two portions). The product was dried under vacuum at 55° C. until constant mass was achieved. Product analysis by HPLC shows 97.5 area % chromatographic purity and 93.3 w/w % potency. Yield— 5.695 kg, 87% (potency corrected)

Pharmacokinetic of Form C and Amorphous (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide in Rat and Dog After once-daily oral administration of Form C as a suspension in 0.5% methylcellulose, 0.1% Tween 80 in purified water, the systemic exposure in rats (both genders) was measured by the $AUC_{(0-24)}$, increased dose-proportionally between 100 and 600 mg/kg. See Table 6. A similar proportionality was observed for the maximal plasma concentration achieved after administration ($C_{max}$).

TABLE 6

| Dose | 100 mg/kg/day | 300 mg/kg/day | 600 mg/kg/day |
|---|---|---|---|
| Cmax (ng/mL) | 6135 | 12835 | 56850 |
| $AUC_{0-24\,h}$ (ng*h/mL) | 19550 | 86450 | 128450 |

After twice-daily oral administration of Form C as a suspension in 0.5% methylcellulose, 0.1% Tween 80 in purified water, the systemic exposure in dogs (both genders) was measured by the $AUC_{(0-24)}$, increased mostly dose-proportionally between 50 and 500 mg/kg BID. See Table 7. The maximum plasma concentration observed after administration, $C_{max}$ also increased with doses. Doses levels ranging from 50 mg/kg to 500 mg/kg were permitted to achieve pharmacological relevant systemic exposures.

TABLE 7

| Dose | 50 mg/kg BID | 150 mg/kg BID | 500 mg/kg BID |
|---|---|---|---|
| Cmax (ng/mL) | 6595 | 21300 | 34150 |
| $AUC_{0-24\,h}$ (ng*h/mL) | 42250 | 176000 | 378000 |

These results are comparable with the material generated for Compound 365 following the procedures outlined in U.S. Patent Publication No. 2015/0011546. Compound 365 was formulated similarly to Form C, suspension in 0.5% methylcellulose, 0.1% Tween 80 in purified water. At both 100 and 300 mpk the Cmax and AUC are slightly superior to what was achieved with Form C. This was expected since the aqueous solubility of Compound 365 is greater than the aqueous solubility of Form C (Table 2). However, the differences in exposure are minimal demonstrating that Form C is mostly equivalent to Compound 365 when administered at these doses in rat. The advantages of Form C compared to the mostly amorphous solid Compound 365 are e.g., isolation and purification (crystallization is a purification step), stability (Form C being the most stable polymorph), and ease to handle/formulate.

TABLE 8

| Dose | 100 mg/kg/day | 300 mg/kg/day |
| --- | --- | --- |
| Cmax (ng/mL) | 7160 | 9810 |
| $AUC_{0\text{-}24\,h}$ (ng*h/mL) | 24200 | 78450 |

While have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. Crystalline Form C of a compound having the formula

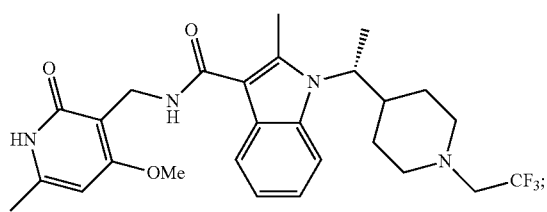 [SMILES: COc1cc(C)[nH]c(=O)c1CNC(=O)c1c(C)n([C@H](C)C2CCN(CC(F)(F)F)CC2)c2ccccc12]

wherein the crystalline form is characterized by at least three X-ray powder diffraction peaks at 2Θ angles selected from 7.56°, 10.24°, 14.18°, 14.38°, 16.26°, 18.04°, 19.60°, and 21.52°.

2. The crystalline Form C of claim 1, characterized by at least four X-ray powder diffraction peaks at 2Θ angles selected from 7.56°, 10.24°, 14.18°, 14.38°, 16.26°, 18.04°, 19.60°, and 21.52°.

3. The crystalline Form C of claim 2, characterized by at least five X-ray powder diffraction peaks at 2Θ angles selected from 7.56°, 10.24°, 14.18°, 14.38°, 16.26°, 18.04°, 19.60°, and 21.52°.

4. The crystalline Form C of claim 3, characterized by at least six X-ray powder diffraction peaks at 2Θ angles selected from 7.56°, 10.24°, 14.18°, 14.38°, 16.26°, 18.04°, 19.60°, and 21.52°.

5. The crystalline Form C of claim 4, characterized by at least seven X-ray powder diffraction peaks at 2Θ angles selected from 7.56°, 10.24°, 14.18°, 14.38°, 16.26°, 18.04°, 19.60°, and 21.52°.

6. The crystalline Form C of claim 5, characterized by X-ray powder diffraction peaks at 2Θ angles selected from 7.56°, 10.24°, 14.18°, 14.38°, 16.26°, 18.04°, 19.60°, and 21.52°.

7. The crystalline Form C of claim 6, characterized by X-ray powder diffraction peaks at 2Θ angles selected from 7.56°, 9.94°, 10.24°, 14.18°, 14.38°, 16.26°, 17.14°, 17.63°, 18.04°, 18.54°, 19.60°, 20.28°, 21.52°, 22.32°, 24.16°, 24.46°, 25.00°, and 27.88°.

8. The crystalline Form C of claim 1, wherein the crystalline form is at least 75% pure by weight.

9. A pharmaceutical composition comprising the crystalline Form C of claim 1, and a pharmaceutically acceptable carrier or diluent.

10. A method of treating a disease or disorder selected from pancreatic cancer, renal cancer, prostate cancer, bladder cancer, breast cancer, colorectal cancer, and non-small lung cancer in a patient in need thereof, comprising the step of administering to said patient the crystalline Form C of claim 1.

11. A process for preparing crystalline Form C of a compound having the formula

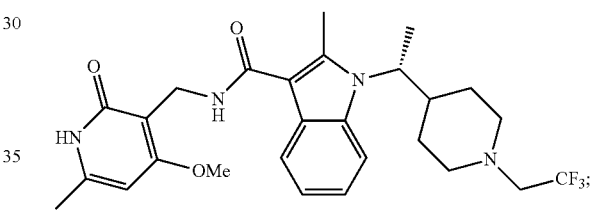

the process comprising agitating a mixture comprising the compound and iPrOAc.

12. The process of claim 11, wherein the mixture is agitated at a temperature of about 65° C.

13. The crystalline Form C of claim 1, wherein the crystalline form is at least 90% pure by weight.

14. The crystalline Form C of claim 1, wherein the crystalline form is at least 95% pure by weight.

15. The crystalline Form C of claim 1, wherein the crystalline form is at least 98% pure by weight.

* * * * *